US007803998B2

(12) United States Patent
Bruce et al.

(10) Patent No.: US 7,803,998 B2
(45) Date of Patent: Sep. 28, 2010

(54) METHODS AND COMPOSITIONS FOR MODIFYING FLOWER DEVELOPMENT

(75) Inventors: Wesley B Bruce, Raleigh, NC (US); Suling Zhao, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 699 days.

(21) Appl. No.: 11/612,518

(22) Filed: Dec. 19, 2006

(65) Prior Publication Data

US 2007/0169225 A1 Jul. 19, 2007

Related U.S. Application Data

(60) Provisional application No. 60/752,674, filed on Dec. 21, 2005.

(51) Int. Cl.
*C12N 15/29* (2006.01)
*C12N 15/82* (2006.01)
*C12N 5/04* (2006.01)
*A01H 5/00* (2006.01)

(52) U.S. Cl. .................... 800/320.1; 800/278; 800/298; 800/290; 800/287; 800/312; 536/23.6; 435/419; 435/320.1

(58) Field of Classification Search ........................ None
See application file for complete search history.

(56) References Cited

U.S. PATENT DOCUMENTS

| 6,460,086 | B1 | 10/2002 | Swaminathan et al. |
| 2003/0079225 | A1 | 4/2003 | Piesing |
| 2003/0233670 | A1* | 12/2003 | Edgerton et al. ............ 800/278 |
| 2005/0050590 | A1 | 3/2005 | Danilevskaya et al. |
| 2006/0269221 | A1 | 11/2006 | Hashimoto et al. |
| 2006/0269222 | A1 | 11/2006 | Horii |
| 2006/0280434 | A1 | 12/2006 | Suzuki et al. |
| 2006/0280444 | A1 | 12/2006 | Kawakami et al. |
| 2006/0290775 | A1 | 12/2006 | Horii et al. |
| 2007/0011357 | A1 | 1/2007 | Watanabe et al. |
| 2007/0022208 | A1 | 1/2007 | Hashimoto et al. |

FOREIGN PATENT DOCUMENTS

| EP | 1445914 | 8/2004 |
| JP | 2003-163850 | 6/2003 |
| WO | 00/78043 | 12/2000 |
| WO | 02/17633 | 2/2002 |
| WO | 03/026301 | 3/2003 |
| WO | 2005/104558 | 11/2005 |

OTHER PUBLICATIONS

Trevaskis et al (2007, Plant Physiology 143:225-235).*
Bowie et al, Science 247:1306-1310, 199.*
McConnell et al, Nature 411 (6838):709-713, 2001.*
Trevaskis, B., et al.; "Short Vegetative Phase-Like MADS-Box Genes Inhibit Floral Meristem Identity in Barley"; Plant Physiology (Jan. 2007) 143:225-235; American Society of Plant Biologists (ASPB); Rockville, MD United States.
de Folter, S., et al.; "Comprehensive Interaction Map of the Arabidopsis MADS Box Transcription Factors"; The Plant Cell (May 2005) 17:1424-1433; American Society of Plant Physiologists; Rockville, MD United States.
Dias, B., et al.; "Unravelling MADS-box gene family in Eucalyptus spp.: A starting pint to an understanding of their developmental role in trees"; Genetics and Molecular Biology (2005) 28(3):501-510; Brazilian Society of Genetics; Brazil.
Nam, J., et al.; "Antiquity and Evolution of the MADS-Box Gene Family Controlling Flower Development in Plants"; Molecular Biology and Evolution (2003) 20(9):1435-1447; Oxford University Press; England.
Petersen, K., et al.; "Two MADS-box genes from perennial ryegrass are regulated by vernalization and involved in the floral transition"; Physiologia Plantarum (2006) 126:268-278; Munksgaard International Publishers LTD; Copenhagen, Denmark.
Pelucchi, N., et al.; "Comparative analysis of rice MADS-box genes expressed during flower development"; Sex Plant Reproduction (2002)15:113-122; Springer-Verlag; Berlin/Heidelberg, Germany.
Genbank Accession No. AJ430635.1, Apr. 15, 2005.
Hartmann, et al., "Molecular cloning of *SVP*: a negative regulator of the floral transition in *Arabidopsis*," The Plant Journal, 2000, vol. 21(4), pp. 351-360.
Kim, et al., "Isolation of MADS-box Genes from Sweet Potato (*Ipomoea batats* (L.) Lam.) Expressed Specifically in Vegetative Tissues," Plant Cell Physiol., 2002, vol. 43(3), pp. 314-322.
Münster, et al., "Maize MADS-Box Genes Galore," Maydica, 2002, vol. 47, pp. 287-301.
Scortecci, et al., "Genetic interactions between FLM and other flowering-time genes in *Arabidopsis thaliana*," Plant Molecular Biology, 2003, vol. 52, pp. 915-922.

* cited by examiner

*Primary Examiner*—Stuart F. Baum
(74) *Attorney, Agent, or Firm*—Alston & Bird LLP

(57) ABSTRACT

The present invention provided methods and compositions for modifying flower development and reproductive development in plants. The methods involve transforming a plant with a polynucleotide construct comprising a promoter operably lined to polynucleotide molecule encoding a short vegetative phase-like transcription factor. The compositions include transformed plants, plant cells, seeds, and expression cassettes comprising a polynucleotide molecule encoding a short vegetative phase-like transcription factor or fragment or variant thereof.

50 Claims, 1 Drawing Sheet

FIGURE 1

```
                    1                                                              70
    ZmSVP1    (1)   ----MA RRE KR ESAA                       LE SV  D A IV S  K SQ A  SMNEII
    ZmSVP2    (1)   ----MA RRE KR ESAA                       Q SV  D A IV S  K SQ A  SMNEII
  OsSVP-like  (1)   ----MA RRE KR ESAA                       E SV  D A IV S  K SH A  SMNEII
    ZmSVP4    (1)   ----MA RRE RR FSAA                       E AV  D A VV A  K SQ A  S N  I
   OsMADS55   (1)   ----MA RRE RR ESAA                       E AV  D A VV S  K SQ A  NMNEII
    ZmSVP3    (1)   MVGTGK RIA RR  NLA                       E S L   E G VV A  K FH A  SMRQ I
    AtSVP     (1)   ----MA KI  RK  NAT                       E SV  D A II S  K FE  C SMKE  
   Consensus  (1)       MARERREIRRIESAAARQVTFSKRRRGLFKKAEELSVLCDADVALIVFSSTGKLSQFASSSMNEII
                    71                                                             140
    ZmSVP1   (67)   DKYSTH KN GKAE--QPSLDLNLEH-SKYANLNEQLVEASLR         E EG SVEE QQL KN
    ZmSVP2   (67)   DKYNTH KN GK E--QPSLDLNLEH-SKYANLNEQLAEASLR         E EG NVEE QQL KN
  OsSVP-like (67)   DKYNTH MN GKAE--QPSLDLNLEH-SKYAHLNEQLAEASLR         E EG S DE QQL KN  A
    ZmSVP4   (67)   DKYSTH KN GK HQ-QPS DLN Q-SKY GLN Q AFF NG             PG SVEE  R  K  A
   OsMADS55  (67)   DKYTTH KN GK DK-QPS DLNLEH-SKC SLNEQLAEASL           E EG SVEE QQM KN  A
    ZmSVP3   (71)   D YD H KT Q  EPQS QLQSH  D-GTCARLKE LAE SL           E QR SVEQ QEL KT
    AtSVP    (67)     NL  KN EKL --QPS EL LVENSD ARK SKE A KSHE          E QG D EE QQL KA  T
   Consensus (71)   DKY THSKNLGKSE  QPSLDLNLEH SKYA LNEQLAEASLRLRQMRGEELEGLSVEELQQLEKNLEAG
                    141                                                            210
    ZmSVP1  (134)    HR LC  DQQF  Q  S EQ ST  AE  RQ RN V  IPPVGK-------------QSV DTENV A
    ZmSVP2  (134)    HR LC  D QF  Q  N ER ST  AE  MQ RN V Q PPAGK-------------QAV DTENV A
  OsSVP-like(134)    HR ML  DQQFM Q  SE QR S   AE  MQ RN V Q SPAEK-------------Q-V DTENE T
    ZmSVP4  (135)    HR  S  DQLFMQQ  F Q GT  F   RR  F   PQ LTAGT-------------MVVA AAEN  T
   OsMADS55 (135)    QR LC  DQQFMQE  SE QR GI  AE  MR RD M QVPTAG-------------LAVPDTENV T
    ZmSVP3  (140)    GS LK   QRI DE  SG EP RT  IE  SR K  V  M SRMET------------Q  ADPEF V
    AtSVP   (135)    TR  E   DKIMSE  SE QK GM  MI   KR RQ G Q TEENERLGMQICNNVHAHGGAE ENAA Y
   Consensus(141)   LHRVL TKDQQFMEQISEL RK TQLAEEN RLRNQVSQI  AG                VADTENVV E
                    211                        251
    ZmSVP1  (191)             VMTALHSGSSQ--DNDDG  V K  G  CV WK-
    ZmSVP2  (191)   E         VMTALHSGSSQ--DNDGG  V K  G   CV WK-
  OsSVP-like(190)   E         VMTALHSGSSQSQDNDDG  V  K G   CG WK-
    ZmSVP4  (193)   D         VMTALHSGSSL--DCDDG      R     -
   OsMADS55 (191)             VMTALNSGSSQ--DNDDG    K G     ------
    ZmSVP3  (196)   E         VTMTS FEPST--D DDC   I   G  LF SK-
    AtSVP   (205)   E          TNAGNSTG P--VD       G   YG ---
   Consensus(211)   EGQSSESVMTALHSGSSQ  DNDDGSDVSLKLGLP  A K
```

US 7,803,998 B2

METHODS AND COMPOSITIONS FOR MODIFYING FLOWER DEVELOPMENT

CROSS REFERENCE

This utility application claims the benefit U.S. Provisional Application No. 60/752,674, filed Dec. 21, 2005, which is incorporated herein by reference.

FIELD OF THE INVENTION

The present invention relates to the fields of genetics and molecular biology, particularly to the regulation of gene expression in plants.

BACKGROUND OF THE INVENTION

Plant biologists have made important strides in recent years in understanding the mechanisms that control flower development in higher plants. A large amount of the recent research on flowering has involved studying the effects of mutations that disrupt, block, or otherwise alter flower development in mutant plants. Most of this research has involved inducing mutations that produce mutant floral phenotypes in the model organism *Arabidopsis thaliana* and then identifying the gene that is responsible for the mutant floral phenotype.

Many of the regulatory genes that have been identified from *Arabidopsis* plants having mutant floral phenotypes are MADS box transcription factors that act at early stages in the organ developmental program (Riechmann and Meyerowitz (1997) *Biol. Chem.* 378:1079-1101; Theiben, et al., (2000) *Plant. Mol. Biol.* 42:115-149). In angiosperms, many of the genes of the MADS family are involved in different steps of flower development, most notably in the determination of floral meristem and organ identity (Riechmann and Meyerowitz (1997) *Biol. Chem.* 378:1079-1101).

While the research on the regulatory genes that control flowering in *Arabidopsis thaliana* and other angiosperms has provided biologists with fundamental knowledge of flower development, additional research on regulatory genes such as MADS box genes is needed to improve our understanding of the unique aspects of flowering in economically important crop plants, particularly those crop plants in which the seeds are the most important component of agricultural yield. Because seeds are produced from flowers, elucidating the biological mechanisms that control flower development in crop plants may lead to strategies for improving agricultural productivity by increasing seed or grain production in important crop plants such as, for example, maize, wheat, rice, soybeans, sunflower, and cotton.

Given the world's increasing human population combined with the ever diminishing amount of the world's land that is available for agricultural, increasing agricultural productivity is a paramount challenge facing humankind. The development of new strategies for the production of improved crop varieties that have increased yield and/or other desirable traits is needed to aid in meeting this paramount challenge.

SUMMARY OF THE INVENTION

The present invention provides compositions and methods for modifying flower development in a plant. The compositions comprise isolated polynucleotide molecules encoding a short vegetative phase (SVP)-like transcription factors from maize and fragments and variants thereof. These methods involve transforming a plant or at least one cell thereof with a polynucleotide construct that comprises a polynucleotide molecule encoding a SVP-like transcription factor of the invention. This SVP-like transcription factor from maize is designated herein as ZmSVP4. The polynucleotide construct further comprises an operably linked promoter that is capable of driving expression of the operably linked polynucleotide molecule in a plant or cell thereof.

The present invention further provides compositions and methods for modifying reproductive development in a plant. The compositions comprise polynucleotide molecules encoding a SVP-like transcription factor of the invention. The methods involve transforming a plant with a polynucleotide construct which comprises a polynucleotide molecule encoding a ZmSVP or fragment or variant thereof. The polynucleotide construct further comprises an operably linked promoter that is capable of driving expression of the operably linked polynucleotide molecule in a plant or cell thereof.

Additionally, the present invention provides compositions and methods for increasing the grain yield of a grain plant. The compositions comprise polynucleotide molecules encoding a SVP-like transcription factor of the invention. The methods comprise transforming a plant with a polynucleotide construct comprising a polynucleotide molecule encoding a ZmSVP or fragment or variant thereof. The polynucleotide construct further comprises an operably linked promoter that is capable of driving expression of the operably linked polynucleotide molecule in a plant or cell thereof. The grain yield of the transformed grain plant is increased when grown under optimal conditions relative to the grain yield of a similar untransformed plant grown under the same conditions.

Also provided are transformed plants, transformed seeds, transformed plant cells, and expression cassettes, each comprising at least one polynucleotide molecule encoding a ZmSVP protein or functional fragment or variant thereof.

BRIEF DESCRIPTION OF THE DRAWING(S)

FIG. 1 is an alignment of the amino acid sequences for ZmSVP4 (SEQ ID NO: 2), AtSVP (Accession No: 30681743, SEQ ID NO: 5) two rice SVP-like proteins (OsSVP-like, Accession No: SCAFFOLD008078_1, Beijing Genomics Institute, SEQ ID NO: 6; OsMADS55, Accession No: 51091146, SEQ ID NO: 7) and three other maize SVP-like genes (ZmSVP1, Accession No: AJ430633, SEQ ID NO: 8; ZmSVP2, Accession No: AJ430693, SEQ ID NO: 9; ZmSVP3, Accession No: AJ430634, SEQ ID NO: 10). A consensus amino acid sequence (SEQ ID NO: 11) is also provided.

DETAILED DESCRIPTION OF THE INVENTION

The present invention is based on the discovery that transforming maize plants with an isolated polynucleotide molecule comprising a nucleotide sequence encoding a maize MADS-box containing, short vegetative phase (SVP)-like transcription factor, designated herein as ZmSVP4, can alter flower development in the transformed plants, when compared to untransformed maize plants. As described in detail below, maize plants that were transformed with a polynucleotide construct comprising a plant constitutive promoter operably linked to a nucleotide sequence encoding the ZmSVP protein produced ears that were substantially larger than ears of plants that were not transformed with this polynucleotide construct. Furthermore, transgenic plants comprising this ZmSVP polynucleotide construct produced ears with significantly more spikelets per row in the ear and had an increased anther density and an increased number of tassel branches.

Compositions of the invention include polynucleotide molecules comprising short vegetative phase-like transcription factors that are involved in regulating gene expression in floral meristems. In particular, the present invention provides for isolated polynucleotide molecules comprising nucleotide sequences encoding the amino acid sequence shown in SEQ ID NO: 2. Further provided are polypeptides having an amino acid sequence encoded by a polynucleotide described herein, for example those set forth in SEQ ID NOS: 1, 3, and 4, and fragments and variants thereof.

The compositions of the present invention find use in methods for modifying flower development in a plant and/or reproductive development in a plant. By "flower development" or "floral development" is intended to mean the development of a flower or inflorescence from the initiation of the floral meristem to the development of the mature flower. By "reproductive development" is intended to mean the development of a flower or inflorescence from the initiation of the floral meristem through pollination and the development of the mature fruit, such as, for example, a maize kernel.

While the present invention is not bound by any particular biological mechanism, it is believed that ZmSVP is involved in controlling and/or maintaining the activity of floral meristems. As disclosed herein below, the ZmSVP gene was discovered to be differentially expressed in the maize ear meristems, depending on the state of meristem activity. In particular, the ZmSVP gene of the present invention was observed to be expressed in the ear meristem when the meristem was producing florets and was downregulated when the meristem had begun to terminate. Furthermore, transgenic maize plants expressing ZmSVP under the control of a constitutive promoter displayed multiple phenotypes that are indicative of an increased period of floral meristem activity in both ears and tassels. In the ears of the transgenic maize plants, an increased number of spikelets per row was detected, relative to control maize plants that were not transformed with the ZmSVP promoter construct. In the tassels of the transgenic maize plants, tassel size, tassel branching, and anther density were all observed to increase relative to control maize plants that were not transformed with the ZmSVP promoter construct. Accordingly, ZmSVP polynucleotide molecules and methods of the present invention find use in modifying flower development and/or reproductive development in a plant. In some embodiments, the methods of the present invention find use in increasing or decreasing the period of time that at least one of floral meristems in a plant is active and/or increasing or decreasing the number of florets initiated in an inflorescence.

In addition, it is expected that by increasing the duration of floral meristem activity in a plant, particularly a grain plant, more particularly a maize plant, the seed or grain yield of the plant will be increased when the plant is grown under optimal conditions. For example, by increasing the number of spikelets per row in a maize ear, the mature maize ear is expected to have a greater number of kernels and thus a larger grain yield per plant when grown under optimal conditions. Accordingly, the compositions and methods of the present invention find use in increasing the number of kernels in an ear of a maize plant.

By "optimal conditions" is intended to mean environmental conditions that allow for the optimal growth and development of a plant of interest. Such favorable environmental conditions include, but are not limited to, optimal quantities of light, water, macronutrients (e.g., N, P, and K) and micronutrients, favorable air and soil temperatures, adequate control of weeds, insects, birds, pathogens and other pests, and optimal planting density. It is recognized that such favorable conditions can include, if necessary, treatment of the plant of interest or the vicinity in which it is growing with one or more pesticides including, but not limited to, herbicides, insecticides, fungicides, nematicides, bactericides, and the like. It is further recognized that the optimal conditions can vary for a particular crop plant species or variety thereof, geographic location, soil characteristics, and/or the time of the year. Furthermore, it is recognized that the methods of the invention do not depend on optimal conditions for the entire growing season. Preferably, the optimal conditions are at least during flower development and/or seed development.

By "yield" or "grain yield" is intended to mean seed or grain yield measured a bushels per acre or metric tons per hectare unless otherwise noted or obvious from the context of use herein. For maize, "yield" or "grain yield" is measured in bushels per acre or metric tons per hectare at 15% grain moisture level unless otherwise noted or obvious from the context of use herein.

Thus, the invention provides methods for modifying flower development in a plant and/or reproductive development in a plant and for increasing seed or grain yield. The methods involve transforming a plant or at least one cell thereof with a polynucleotide construct that comprises a polynucleotide molecule encoding an SVP-like transcription factor of the invention. This SVP-like transcription factor from maize is designated herein as ZmSVP4. The polynucleotide construct further comprises an operably linked promoter that is capable of driving expression of the operably linked polynucleotide molecule in a plant or cell thereof. The methods further involve regenerating a transformed plant from the transformed plant cell. Relative to an untransformed plant, the plants produced by the methods of the invention display modified flower development, modified reproductive development, and/or increased seed or grain yield.

In one embodiment, the methods of the invention can be used to produce a transformed maize plant with an ear that has more spikelets per row than an untransformed maize plant without affecting the number of rows of spikelets (around the circumference) on the developing ears. The transformed maize plant is produced by introducing into at least one maize cell a polynucleotide construct comprising a promoter that is expressed in a plant cell operably linked to a nucleotide sequence encoding ZmSVP or functional fragment or variant thereof, and then regenerating a transformed maize plant therefrom. Optimally, the promoter drives expression of the operably linked ZmSVP nucleotide sequence of the present invention in the maize floral tissues, particularly in the ear, more particularly in the ear when the floral meristem is active. Relative to an untransformed plant, the transformed maize plant of this embodiment comprises modified flower development, particularly an increase in spikelets per row in the ear, more particularly an increase in spikelets per row while maintaining the same number of rows per ear. When grown under optimal conditions, this transformed maize plant is expected to display increase grain yield per plant, when compared to the grain yield of an untransformed maize plant.

The methods of the present invention encompass plants that are transformed with one or more other polynucleotides in addition to a ZmSVP of the present invention. Such polynucleotides can, for example, when operably linked to a promoter expressible in a plant cause further increases in grain yield in the transformed plant by reducing kernel tip abortion, enhancing reproductive sink strength, and/or altering other developmental processes that would lead to increased reproductive growth. For example, a plant can be transformed with an endosperm and/or pedicel-specific promoter can be operably linked to driving a cell-wall invertase coding sequence (see, references cited in Bruce, et al., (2002) *J. Exp. Bot.* 53:13-25). Alternatively or additionally, the plant can be transformed with ACC synthase-RNAi, or a mutant line with knock-out of the maize ACC synthase gene can be used in the methods of the present invention (Young, et al., (2004) *Plant J.* 40:813-25).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5% or 1% (by dry weight) of contaminating protein. When the protein of the invention or biologically active portion thereof is recombinantly produced, optimally culture medium represents less than about 30%, 20%, 10%, 5% or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of a polynucleotide may encode protein fragments that retain biological activity of the native protein and hence ZmSVP activity. Alternatively, fragments of a polynucleotide that are useful as hybridization probes generally do not encode fragment proteins retaining biological activity. Thus, fragments of a nucleotide sequence may range from at least about 20 nucleotides, about 50 nucleotides, about 100 nucleotides and up to the full-length polynucleotide encoding the proteins of the invention.

A fragment of an polynucleotide that encodes a biologically active portion of an ZmSVP protein of the invention will encode at least 15, 25, 30, 50, 100, 150 or 200 contiguous amino acids, or up to the total number of amino acids present in a full-length ZmSVP protein of the invention (for example, 225 amino acids for SEQ ID NO: 2). Fragments of a ZmSVP polynucleotide molecule that are useful as hybridization probes or PCR primers generally need not encode a biologically active portion of an ZmSVP protein.

Thus, a fragment of a ZmSVP polynucleotide molecule of the present invention may encode a biologically active portion of a ZmSVP protein, or it may be a fragment that can be used as a hybridization probe or PCR primer using methods disclosed below. A biologically active portion of a ZmSVP protein can be prepared by isolating a portion of one of the ZmSVP polynucleotide molecules of the invention, expressing the encoded portion of the ZmSVP protein (e.g., by recombinant expression in vitro), and assessing the activity of the encoded portion of the ZmSVP protein. Polynucleotide molecules that are fragments of a ZmSVP nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,750, 2,000, 2,500, 3,000, 3,500, 4,000, 4,500, 5,000, 6,000, 7,000, 8,000, 9,000 or 10,000 contiguous nucleotides, or up to the number of nucleotides present in a full-length ZmSVP polynucleotide molecule disclosed herein (for example, 1,041, 675, and 10,615 nucleotides for SEQ ID NOS: 1, 3 and 4, respectively).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the ZmSVP polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode a ZmSVP protein of the invention. Generally, variants of a particular polynucleotide of the invention will have at least about 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO: 2 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, ZmSVP activity as described herein. Such variants may result from, for example, genetic polymorphism or from human manipulation. Biologically active variants of a native ZmSVP protein of the invention will have at least about 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2 or even 1 amino acid residue.

The proteins of the invention may be altered in various ways including amino acid substitutions, deletions, truncations, and insertions. Methods for such manipulations are generally known in the art. For example, amino acid sequence variants and fragments of the ZmSVP proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel, et al., (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired ZmSVP activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequence encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays for ZmSVP activity. That is, the activity can be evaluated by transforming a plant with a polynucleotide encoding a ZmSVP protein operably linked to a promoter that drives expression in the plant and monitoring the effect on floral phenotypes relative to the floral phenotypes of a control plant that is not transformed with the polynucleotide encoding a ZmSVP protein. See, Example 2 below.

By "ZmSVP activity" is intended to mean the ability when such a polypeptide is overexpressed in a plant to cause at least one modification in flower development. Such modifications in flower development include, for example, an increase in the number of florets initiated in an inflorescence, an increase in the period of time that a floral meristem is active, an increase in anther density, and tassel branch number. In maize plants, such modifications in flower development include, but at not limited to, an increase in floret number per ear, an increase in spikelets per row in the ear without adversely affecting the number of rows of spikelets, an increase in the number of kernels per ear, an increase in floret number per tassel, an increase in tassel size, an increase in the number of branches per tassel, and an increase in anther density in the tassel, and an increase in tassel branch numbers.

ZmSVP activity can be evaluated, for example, by transforming a plant with a promoter expressible in a plant operably linked to a polynucleotide molecule encoding a ZmSVP protein of the invention or fragment or variant thereof, and then monitoring flower development in the transformed plant, particularly for any of the modifications in flower development described above or elsewhere in the present disclosure. Optimally, the promoter drives in expression a flower or part thereof, particularly a floral meristem. Such promoters include, but are not limited to, constitutive, chemical-regulated, flower-preferred, floral meristem-preferred, ear meristem-preferred, and tassel meristem-preferred promoters.

Variant polynucleotides and proteins also encompass sequences and proteins derived from a mutagenic and recombinogenic procedure such as DNA shuffling. With such a procedure, one or more different ZmSVP coding sequences can be manipulated to create a new ZmSVP polynucleotide molecule that encodes a protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the ZmSVP gene of the invention and other known SVP, other MADS genes or other transcription factors to obtain a new gene coding for a protein with an improved property of interest, such as an increased binding affinities to target cis-elements in the case of DNA-binding factors, increased or decreased binding affinities to factors that make contact with the SVP4 domains or increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291; and U.S. Pat. Nos. 5,605,793 and 5,837,458.

The polynucleotides of the invention can be used to isolate corresponding sequences from other organisms, particularly other plants, more particularly other monocots. In this manner, methods such as PCR, hybridization, and the like can be used to identify such sequences based on their sequence homology to the sequence[s] set forth herein. Sequences isolated based on their sequence identity to the entire ZmSVP sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99% or greater sequence identity. Functions of orthologs are often highly conserved among species. Thus, isolated polynucleotides that encode for a SVP4 protein and which hybridize under stringent conditions to the ZmSVP polynucleotide molecules disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also, Innis, et al., eds. (1990) *PCR Protocols: A Guide to Methods and Applications* (Academic Press, New York); Innis and Gelfand, eds. (1995) *PCR Strategies*

(Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the ZmSVP polynucleotide molecules of the invention. Methods for preparation of probes for hybridization and for construction of cDNA and genomic libraries are generally known in the art and are disclosed in Sambrook, et al., (1989) *Molecular Cloning: A Laboratory Manual* (2d ed., Cold Spring Harbor Laboratory Press, Plainview, N.Y.).

For example, the entire ZmSVP polynucleotide molecule disclosed herein, or one or more portions thereof, may be used as a probe capable of specifically hybridizing to corresponding molecules polynucleotide molecule and messenger RNAs. To achieve specific hybridization under a variety of conditions, such probes include sequences that are unique among molecules polynucleotide sequences and are optimally at least about 10 nucleotides in length, and most optimally at least about 20 nucleotides in length. Such probes may be used to amplify corresponding ZmSVP polynucleotide molecules from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith, et al., (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65; and Pearson, et al., (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul, et al., (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see, Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The ZmSVP polynucleotide molecule of the invention can be provided in expression cassettes for expression in the plant of interest. The cassette will include 5' and 3' regulatory sequences operably linked to a ZmSVP polynucleotide molecule of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the ZmSVP polynucleotide molecule to be under the transcriptional regulation of the regulatory regions. The expression cassette may additionally contain selectable marker genes.

The expression cassette will include in the 5'-3' direction of transcription, a transcriptional and translational initiation region (i.e., a promoter), a ZmSVP polynucleotide molecule of the invention, and a transcriptional and translational termination region (i.e., termination region) functional in plants. The regulatory regions (i.e., promoters, transcriptional regulatory regions, and translational termination regions) and/or the ZmSVP polynucleotide molecule of the invention may be native/analogous to the host cell or to each other. Alternatively, the regulatory regions and/or the ZmSVP polynucleotide molecule of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

While it may be optimal to express the sequences using heterologous promoters, the native promoter sequences may be used. Such constructs can change expression levels of ZmSVP in the plant or plant cell. Thus, the phenotype of the plant or plant cell can be altered.

The termination region may be native with the transcriptional initiation region, may be native with the operably linked a ZmSVP polynucleotide molecule of interest, may be native with the plant host, or may be derived from another source (i.e., foreign or heterologous) to the promoter, the ZmSVP polynucleotide molecule of interest, the plant host, or any combination thereof. Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray, et al., (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus) (*Virology* 154:9-20), and human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, N.Y.), pp. 237-256); and maize chlorotic mottle virus leader (MCMV) (Lommel, et al., (1991) *Virology* 81:382-385). See also, Della-Cioppa, et al., (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention, including the native promoter of the polynucleotide sequence of interest. The promoters can be selected based on the desired outcome.

The nucleic acids can be combined with tissue-preferred, chemical-regulated, or other promoters for expression in plants.

Tissue-preferred promoters can be utilized to target enhanced ZmSVP expression within a particular plant tissue. Tissue-preferred promoters include Yamamoto, et al., (1997) *Plant J.* 12(2):255-265; Kawamata, et al., (1997) *Plant Cell Physiol.* 38(7):792-803; Hansen, et al., (1997) *Mol. Gen Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam (1994) *Results Probl. Cell Differ.* 20:181-196; Orozco, et al., (1993) *Plant Mol Biol.* 23(6): 1129-1138; Matsuoka, et al., (1993) *Proc Natl. Acad. Sci. USA* 90(20):9586-9590; and Guevara-Garcia, et al., (1993) *Plant J.* 4(3):495-505. Such promoters can be modified, if necessary, for weak expression.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257), the ethanol/alcohol-inducible promoter (Deveaux, et al., (2003) *Plant J.* 36(6):918-30), the copper-inducible promoter MRE (Mett, et al., (1993) *Proc. Natl. Acad. Sci. USA* 90:4567-4571), and tetracycline-inducible and tetracycline-repressible promoters (see, for example, Gatz, et al., (1991) *Mol. Gen. Genet.* 227:229-237, and U.S. Pat. Nos. 5,814,618 and 5,789,156), herein incorporated by reference.

Constitutive promoters include, for example, the core promoter of the Rsyn7 promoter and other constitutive promoters disclosed in WO 99/43838 and U.S. Pat. No. 6,072,050; the core CaMV 35S promoter (Odell, et al., (1985) *Nature* 313: 810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Where low-level expression is desired, weak promoters will be used. Generally, by "weak promoter" is intended a promoter that drives expression of a coding sequence at a low level. By low level is intended at levels of about $1/1000$ transcripts to about $1/100,000$ transcripts to about $1/500,000$ transcripts. Alternatively, it is recognized that weak promoters also encompasses promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su, et al., (2004) *Biotechnol Bioeng* 85:610-9 and Fetter, et al., (2004) *Plant Cell* 16:215-28), cyan florescent protein (CYP) (Bolte, et al., (2004) *J. Cell Science* 117:943-54 and Kato, et al., (2002) *Plant Physiol* 129:913-42), and yellow florescent protein (PhiYFP™ from Evrogen, see, Bolte, et al., (2004) *J. Cell Science* 117:943-54). For additional selectable markers, see generally, Yarranton (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Aci. USA* 86:5400-5404; Fuerst, et al., (1989) *Proc. Natl. Acad. Sci. USA* 86:2549-2553; Deuschle, et al., (1990) *Science* 248: 480-483; Gossen (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin); Gill, et al., (1988) *Nature* 334:721-724. Such disclosures are herein incorporated by reference.

The above list of selectable marker genes is not meant to be limiting. Any selectable marker gene can be used in the present invention.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway, et al., (1986) *Biotechniques* 4:320-334), electroporation (Riggs, et al., (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski, et al., (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, U.S. Pat. No. 5,932,782; Tomes, et al., (1995) in *Plant Cell, Tissue, and Organ Culture: Fundamental Methods*, ed. Gamborg and Phillips (Springer-Verlag, Berlin); McCabe, et al., (1988) *Biotechnology* 6:923-926); and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783; and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature (London)* 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, N.Y.), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the ZmSVP sequences of the invention can be provided to a plant using a variety of transient transformation methods. Such transient transformation methods include, but are not limited to, the introduction of the ZmSVP protein or variants and fragments thereof directly into the plant or the introduction of the ZmSVP transcript into the plant. Such methods include, for example, microinjection or particle bombardment. See, for example, Crossway, et al., (1986) *Mol Gen. Genet* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784, all of which are herein incorporated by reference. Alternatively, the ZmSVP polynucleotide molecule can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the a ZmSVP protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191; 5,889,190; 5,866,785; 5,589,367; 5,316,931 and Porta, et al., (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

Pedigree breeding starts with the crossing of two genotypes, such as an elite line of interest and one other elite inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→$F_5$, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant gene or transgene conferring a desired trait (e.g., modified flower development, modified reproductive development, increased grain yield) and selecting an F1 progeny plant comprising the mutant gene or transgene conferring the desired trait, and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of elite lines that comprises such mutations.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza* sativa), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

A "subject plant or plant cell" is one in which genetic alteration, such as transformation, has been effected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

A method for modulating the concentration and/or activity of the polypeptide of the present invention in a plant is provided. In general, concentration and/or activity is increased or decreased by at least 1%, 5%, 10%, 20%, 30%, 40%, 50%, 60%, 70%, 80% or 90% relative to a native control plant, plant part, or cell which did not have the sequence of the invention introduced. Modulation in the present invention may occur during and/or subsequent to growth of the plant to the desired stage of development. In specific embodiments, the polypeptides of the present invention are modulated in monocots, particularly maize.

The expression level of the ZmSVP polypeptide may be measured directly, for example, by assaying for the level of the ZmSVP polypeptide in the plant, or indirectly, for example, by measuring the ZmSVP activity of the ZmSVP polypeptide in the plant. Methods for determining ZmSVP activity are described elsewhere herein.

In specific embodiments, the polypeptide or the polynucleotide of the invention is introduced into the plant cell. Subsequently, a plant cell having the introduced sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

It is also recognized that the level and/or activity of the polypeptide may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such nucleotide constructs and methods of use are known in the art. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham, et al., (1999) *Proc. Natl. Acad. Sci. USA* 96:8774-8778; herein incorporated by reference.

It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of the polynucleotide into a cell. For example, the polynucleotide, or any part thereof, may incorporate into the genome of the plant. Alterations to the genome of the present invention include, but are not limited to, additions, deletions, and substitutions of nucleotides into the genome. While the methods of the present invention do not depend on additions, deletions, and substitutions of any particular number of nucleotides, it is recognized that such additions, deletions, or substitutions comprises at least one nucleotide.

In one embodiment, the activity and/or level of the ZmSVP polypeptide of the invention is increased. An increase in the level and/or activity of the ZmSVP polypeptide of the invention can be achieved by providing to the plant a ZmSVP polypeptide. As discussed elsewhere herein, many methods are known the art for providing a polypeptide to a plant including, but not limited to, direct introduction of the polypeptide into the plant, introducing into the plant (transiently or stably) a polynucleotide construct encoding a polypeptide having ZmSVP activity. It is also recognized that the methods of the invention may employ a polynucleotide that is not capable of directing, in the transformed plant, the expression of a protein or an RNA. Thus, the level and/or activity of a ZmSVP polypeptide may be increased by altering the gene encoding the ZmSVP polypeptide or its promoter. See, e.g., Kmiec, U.S. Pat. No. 5,565,350; Zarling, et al., PCT/US93/03868. Therefore mutagenized plants that carry mutations in ZmSVP genes, where the mutations increase expression of the ZmSVP gene or increase the ZmSVP activity of the encoded ZmSVP polypeptide are provided.

In other embodiments, the activity and/or level of the ZmSVP polypeptide of the invention is reduced or eliminated by introducing into a plant a polynucleotide that inhibits the level or activity of the ZmSVP polypeptide of the invention. The polynucleotide may inhibit the expression of ZmSVP directly, by preventing translation of the ZmSVP messenger RNA, or indirectly, by encoding a polypeptide that inhibits the transcription or translation of a ZmSVP gene encoding a ZmSVP protein. Methods for inhibiting or eliminating the expression of a gene in a plant are well known in the art, and any such method may be used in the present invention to inhibit the expression of ZmSVP in a plant. In other embodiments of the invention, the activity of the ZmSVP polypeptide is reduced or eliminated by transforming a plant cell with an sequence encoding a polypeptide that inhibits the activity of the ZmSVP polypeptide. In other embodiments, the activity of a ZmSVP polypeptide may be reduced or eliminated by disrupting the gene encoding the ZmSVP polypeptide. The invention encompasses mutagenized plants that carry mutations in ZmSVP genes, where the mutations reduce expression of the ZmSVP gene or inhibit the ZmSVP activity of the encoded ZmSVP polypeptide.

Reduction of the activity of specific genes (also known as gene silencing or gene suppression) is desirable for several aspects of genetic engineering in plants. Many techniques for gene silencing are well known to one of skill in the art, including, but not limited to, antisense technology (see, e.g., Sheehy, et al., (1988) Proc. Natl. Acad. Sci. USA 85:8805-8809; and U.S. Pat. Nos. 5,107,065; 5,453,566; and 5,759,829); cosuppression (e.g., Taylor (1997) Plant Cell 9:1245; Jorgensen (1990) Trends Biotech. 8(12):340-344; Flavell (1994) Proc. Natl. Acad. Sci. USA 91:3490-3496; Finnegan, et al., (1994) Bio/Technology 12:883-888; and Neuhuber, et al., (1994) Mol. Gen. Genet. 244:230-241); RNA interference (Napoli, et al., (1990) Plant Cell 2:279-289; U.S. Pat. No. 5,034,323; Sharp (1999) Genes Dev. 13:139-141; Zamore, et al., (2000) Cell 101:25-33; and Montgomery, et al., (1998) Proc. Natl. Acad. Sci. USA 95:15502-15507), virus-induced gene silencing (Burton, et al., (2000) Plant Cell 12:691-705; and Baulcombe (1999) Curr. Op. Plant Bio. 2:109-113); target-RNA-specific ribozymes (Haseloff, et al., (1988) Nature 334:585-591); hairpin structures (Smith, et al., (2000) Nature 407:319-320; WO 99/53050; WO 02/00904; WO 98/53083; Chuang and Meyerowitz (2000) Proc. Natl. Acad. Sci. USA 97:4985-4990; Stoutjesdijk, et al., (2002) Plant Physiol. 129:1723-1731; Waterhouse and Helliwell (2003) Nat. Rev. Genet. 4:29-38; Pandolfini, et al., BMC Biotechnology 3:7, U.S. Patent Publication No. 20030175965; Panstruga, et al., (2003) Mol. Biol. Rep. 30:135-140; Wesley, et al., (2001) Plant J. 27:581-590; Wang and Waterhouse (2001) Curr. Opin. Plant Biol. 5:146-150; U.S. Patent Publication No. 20030180945; and, WO 02/00904, all of which are herein incorporated by reference); ribozymes (Steinecke, et al., (1992) EMBO J. 11:1525; and Perriman, et al., (1993) Antisense Res. Dev. 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes, et al., (1999) Trends Plant Sci. 4:90-96; Dharmapuri and Sonti (1999) FEMS Microbiol. Lett. 179:53-59; Meissner, et al., (2000) Plant J. 22:265-274; Phogat, et al., (2000) J Biosci. 25:57-63; Walbot (2000) Curr. Opin. Plant Biol. 2:103-107; Gai, et al., (2000) Nucleic Acids Res. 28:94-96; Fitzmaurice, et al., (1999) Genetics 153:1919-1928; Bensen, et al., (1995) Plant Cell 7:75-84; Mena, et al., (1996) Science 274:1537-1540; and U.S. Pat. No. 5,962,764); each of which is herein incorporated by reference; and other methods or combinations of the above methods known to those of skill in the art.

The methods of the invention find use in modifying flower and/or reproductive development so as to decrease the number of florets produced by a floral meristem of a plant. These methods involve genetically modifying a plant, particularly a maize plant, to reduce or eliminate the activity of the ZmSVP protein or ortholog thereof. Such methods find use in the production of plants for use in hybrid seed. In one embodiment of the invention, maize plants are produced that have a reduced number or no florets in the tassel. In another embodiment, maize plants are produced that have a reduced number or no florets in the ear.

In yet another embodiment of the invention, a maize plant comprising altered flower development is produced by a method comprising the steps of (a) transforming a maize plant cell with at least one expression cassette capable of expressing a polynucleotide that reduces or eliminates the activity of the expression of the ZmSVP protein in a maize plant or part thereof; and (b) regenerating a transformed maize plant from the transformed maize plant cell of step (a). The expression cassette comprises a promoter the drives expression in a plant, optimally in a floral meristem of a plant, more optimally in a in a floral meristem of a maize plant, most optimally in tassel or ear meristem of a maize plant.

To reduce or eliminate the expression of ZmSVP or ortholog thereof, it is recognized that with the polynucleotides of the invention, antisense constructions, complementary to at least a portion of the messenger RNA (mRNA) for the ZmSVP sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used.

The polynucleotides of the present invention may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a polynucleotide that corresponds to the transcript of the endogenous gene. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference. Thus, many methods may be used to reduce or eliminate the activity of a ZmSVP polypeptide. More than one method may be used to reduce the activity of a single ZmSVP polypeptide. In addition, combinations of methods may be employed to reduce or eliminate the activity of the ZmSVP polypeptides.

In some embodiments, the activity of the ZmSVP protein is reduced or eliminated by transforming a plant cell with an expression cassette that expresses a polynucleotide that inhibits the expression of the ZmSVP protein. The polynucleotide may inhibit the expression of ZmSVP protein directly, by preventing translation of the ZmSVP messenger RNA, or indirectly, by encoding a polypeptide that inhibits the transcription or translation of a ZmSVP gene encoding a ZmSVP protein. Methods for inhibiting or eliminating the expression of a gene in a plant are well known in the art, and any such method may be used in the present invention to inhibit the expression of ZmSVP protein in a plant, particularly a maize plant.

In accordance with the present invention, the expression of a ZmSVP protein is inhibited if the protein level of the ZmSVP protein is statistically lower than the protein level of the same ZmSVP protein in a plant that has not been genetically modified or mutagenized to inhibit the expression of that ZmSVP protein. In particular embodiments of the invention, the protein level of the ZmSVP protein in a modified plant according to the invention is less than 95%, less than 90%, less than 80%, less than 70%, less than 60%, less than 50%, less than 40%, less than 30%, less than 20%, less than 10%, or less than 5% of the protein level of the same ZmSVP protein in a plant that is not a mutant or that has not been genetically modified to inhibit the expression of that ZmSVP protein. The expression level of the ZmSVP protein may be measured directly, for example, by assaying for the level of ZmSVP protein expressed in the ZmSVP protein cell or plant, or indirectly, for example, by measuring the ZmSVP activity of the ZmSVP protein in the plant or cell thereof. Methods for determining the ZmSVP activity of ZmSVP protein are described elsewhere herein.

In other embodiments of the invention, the activity of ZmSVP protein is reduced or eliminated by transforming a cell of the plant of interest with an expression cassette comprising a polynucleotide encoding a polypeptide that inhibits the activity of the ZmSVP protein. The ZmSVP activity of a ZmSVP protein is inhibited according to the present invention if the ZmSVP activity of the ZmSVP protein is statistically lower the ZmSVP activity of the same ZmSVP protein in a plant that has not been genetically modified to inhibit the ZmSVP activity of that ZmSVP protein. In particular embodiments of the invention, the ZmSVP activity of the ZmSVP protein in a modified plant according to the invention is less than 95%, less than 90%, less than 80%, less than 70%, less than 60%, less than 50%, less than 40%, less than 30%, less than 20%, less than 10% or less than 5% of the ZmSVP activity of the same ZmSVP protein in a plant that that has not been genetically modified to inhibit the expression of that ZmSVP protein. The ZmSVP activity of a ZmSVP protein is "eliminated" according to the invention when it is not detectable by the assay methods described elsewhere herein. Methods of determining the ZmSVP activity of a ZmSVP protein are described elsewhere herein.

In other embodiments, the activity of a ZmSVP protein may be reduced or eliminated by disrupting the gene encoding the ZmSVP protein. The invention encompasses mutagenized ZmSVP protein plants that carry mutations in ZmSVP genes, where the mutations reduce expression of the ZmSVP gene or inhibit the ZmSVP activity of the encoded ZmSVP protein.

Thus, many methods may be used to reduce or eliminate the activity of a ZmSVP protein. More than one method may be used to reduce the activity of a single ZmSVP protein. In addition, combinations of methods may be employed to reduce or eliminate the activity of two or more different ZmSVP proteins.

Non-limiting examples of methods of reducing or eliminating the expression of a ZmSVP protein are given below.

A. Polynucleotide-Based Methods

In some embodiments of the present invention, a plant cell is transformed with an expression cassette that is capable of expressing a polynucleotide that inhibits the expression of ZmSVP protein. The term "expression" as used herein refers to the biosynthesis of a gene product, including the transcription and/or translation of said gene product. For example, for the purposes of the present invention, an expression cassette capable of expressing a polynucleotide that inhibits the expression of at least one ZmSVP protein is an expression cassette capable of producing an RNA molecule that inhibits the transcription and/or translation of at least one ZmSVP protein. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a ZmSVP protein are given below.

1. Sense Suppression/Cosuppression

In some embodiments of the invention, inhibition of the expression of ZmSVP protein may be obtained by sense suppression or cosuppression. For cosuppression, an expression cassette is designed to express an RNA molecule corresponding to all or part of a messenger RNA encoding a ZmSVP protein in the "sense" orientation. Overexpression of the RNA molecule can result in reduced expression of the native gene. Accordingly, multiple plant lines transformed with the cosuppression expression cassette are screened to identify those that show the greatest inhibition of ZmSVP protein expression.

The polynucleotide used for cosuppression may correspond to all or part of the sequence encoding the ZmSVP protein, all or part of the 5' and/or 3' untranslated region of a ZmSVP protein transcript, or all or part of both the coding sequence and the untranslated regions of a transcript encoding ZmSVP protein. In some embodiments where the polynucleotide comprises all or part of the coding region for the ZmSVP protein, the expression cassette is designed to eliminate the start codon of the polynucleotide so that no protein product will be transcribed.

Cosuppression may be used to inhibit the expression of plant genes to produce plants having undetectable protein levels for the proteins encoded by these genes. See, for example, Broin, et al., (2002) Plant Cell 14:1417-1432.

Cosuppression may also be used to inhibit the expression of multiple proteins in the same plant. See, for example, U.S. Pat. No. 5,942,657. Methods for using cosuppression to inhibit the expression of endogenous genes in plants are described in Flavell, et al., (1994) *Proc. Natl. Acad. Sci. USA* 91:3490-3496; Jorgensen, et al., (1996) *Plant Mol. Biol.* 31:957-973; Johansen and Carrington (2001) *Plant Physiol.* 126:930-938; Broin, et al., (2002) *Plant Cell* 14:1417-1432; Stoutjesdijk, et al., (2002) *Plant Physiol.* 129:1723-1731; Yu, et al., (2003) *Phytochemistry* 63:753-763; and U.S. Pat. Nos. 5,034,323, 5,283,184, and 5,942,657; each of which is herein incorporated by reference. The efficiency of cosuppression may be increased by including a poly-dT region in the expression cassette at a position 3' to the sense sequence and 5' of the polyadenylation signal. See, U.S. Patent Publication No. 20020048814, herein incorporated by reference. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference.

2. Antisense Suppression

In some embodiments of the invention, inhibition of the expression of the ZmSVP protein may be obtained by antisense suppression. For antisense suppression, the expression cassette is designed to express an RNA molecule complementary to all or part of a messenger RNA encoding the ZmSVP protein. Overexpression of the antisense RNA molecule can result in reduced expression of the native gene. Accordingly, multiple plant lines transformed with the antisense suppression expression cassette are screened to identify those that show the greatest inhibition of ZmSVP protein expression.

The polynucleotide for use in antisense suppression may correspond to all or part of the complement of the sequence encoding the ZmSVP protein, all or part of the complement of the 5' and/or 3' untranslated region of the ZmSVP protein transcript, or all or part of the complement of both the coding sequence and the untranslated regions of a transcript encoding the ZmSVP protein. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same plant. See, for example, U.S. Pat. No. 5,942,657. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used. Methods for using antisense suppression to inhibit the expression of endogenous genes in plants are described, for example, in Liu, et al., (2002) *Plant Physiol.* 129:1732-1743 and U.S. Pat. Nos. 5,759,829 and 5,942,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020048814, herein incorporated by reference.

3. Double-Stranded RNA Interference

In some embodiments of the invention, inhibition of the expression of a ZmSVP protein may be obtained by double-stranded RNA (dsRNA) interference. For dsRNA interference, a sense RNA molecule like that described above for cosuppression and an antisense RNA molecule that is fully or partially complementary to the sense RNA molecule are expressed in the same cell, resulting in inhibition of the expression of the corresponding endogenous messenger RNA.

Expression of the sense and antisense molecules can be accomplished by designing the expression cassette to comprise both a sense sequence and an antisense sequence. Alternatively, separate expression cassettes may be used for the sense and antisense sequences. Multiple plant lines transformed with the dsRNA interference expression cassette or expression cassettes are then screened to identify plant lines that show the greatest inhibition of ZmSVP protein expression. Methods for using dsRNA interference to inhibit the expression of endogenous plant genes are described in Waterhouse, et al., (1998) *Proc. Natl. Acad. Sci. USA* 95:13959-13964, Liu, et al., (2002) *Plant Physiol.* 129:1732-1743, and WO 99/49029, WO 99/53050, WO 99/61631, and WO 00/49035; each of which is herein incorporated by reference.

4. Hairpin RNA Interference and Intron-Containing Hairpin RNA Interference

In some embodiments of the invention, inhibition of the expression of the ZmSVP protein may be obtained by hairpin RNA (hpRNA) interference or intron-containing hairpin RNA (ihpRNA) interference. These methods are highly efficient at inhibiting the expression of endogenous genes. See, Waterhouse and Helliwell (2003) *Nat. Rev. Genet.* 4:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations of plants. See, for example, Chuang and Meyerowitz (2000) *Proc. Natl. Acad. Sci. USA* 97:4985-4990; Stoutjesdijk, et al., (2002) *Plant Physiol.* 129:1723-1731; and Waterhouse and Helliwell (2003) *Nat. Rev. Genet.* 4:29-38. Methods for using hpRNA interference to inhibit or silence the expression of genes are described, for example, in Chuang and Meyerowitz (2000) *Proc. Natl. Acad. Sci. USA* 97:4985-4990; Stoutjesdijk, et al., (2002) *Plant Physiol.* 129:1723-1731; Waterhouse and Helliwell (2003) *Nat. Rev. Genet.* 4:29-38; Pandolfini, et al., *BMC Biotechnology* 3:7, and U.S. Patent Publication No. 20030175965; each of which is herein incorporated by reference. A transient assay for the efficiency of hpRNA constructs to silence gene expression in vivo has been described by Panstruga, et al., (2003) *Mol. Biol. Rep.* 30:135-140, herein incorporated by reference.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, and this increases the efficiency of interference. See, for example, Smith, et al., (2000) *Nature* 407:319-320. In fact, Smith, et al., show 100% suppression of endogenous gene expression using ihpRNA-mediated interference. Methods for using ihpRNA interference to inhibit the expression of endogenous plant genes are described, for example, in Smith, et al., (2000) *Nature* 407:319-320; Wesley, et al., (2001) *Plant J.* 27:581-590; Wang and Waterhouse (2001) *Curr. Opin. Plant Biol.* 5:146-150; Waterhouse and Helliwell (2003) *Nat. Rev. Genet.* 4:29-38; Helliwell and Waterhouse (2003) *Methods* 30:289-295, and U.S. Patent Publication No. 20030180945, each of which is herein incorporated by reference.

The expression cassette for hpRNA interference may also be designed such that the sense sequence and the antisense sequence do not correspond to an endogenous RNA. In this embodiment, the sense and antisense sequence flank a loop sequence that comprises a nucleotide sequence corresponding to all or part of the endogenous messenger RNA of the target gene. Thus, it is the loop region that determines the specificity of the RNA interference. See, for example, WO 02/00904, herein incorporated by reference.

Transcriptional gene silencing (TGS) may be accomplished through use of hpRNA constructs wherein the inverted repeat of the hairpin shares sequence identity with the promoter region of a gene to be silenced. Processing of the hpRNA into short RNAs which can interact with the homologous promoter region may trigger degradation or methylation to result in silencing (Aufsatz, et al., (2002) *PNAS* 99 (Suppl. 4):16499-16506; Mette, et al., (2000) *EMBO J* 19(19):5194-5201).

5. Amplicon-Mediated Interference

Amplicon expression cassettes comprise a plant virus-derived sequence that contains all or part of the target gene but generally not all of the genes of the native virus. The viral sequences present in the transcription product of the expression cassette allow the transcription product to direct its own replication. The transcripts produced by the amplicon may be either sense or antisense relative to the target sequence (i.e., the messenger RNA for the ZmSVP protein). Methods of using amplicons to inhibit the expression of endogenous plant genes are described, for example, in Angell and Baulcombe (1997) *EMBO J.* 16:3675-3684, Angell and Baulcombe (1999) *Plant J.* 20:357-362, and U.S. Pat. No. 6,646,805, each of which is herein incorporated by reference.

6. Ribozymes

In some embodiments, the polynucleotide expressed by the expression cassette of the invention is catalytic RNA or has ribozyme activity specific for the messenger RNA of the ZmSVP protein. Thus, the polynucleotide causes the degradation of the endogenous messenger RNA, resulting in reduced expression of the ZmSVP protein. This method is described, for example, in U.S. Pat. No. 4,987,071, herein incorporated by reference.

7. Small Interfering RNA or Micro RNA

In some embodiments of the invention, inhibition of the expression of the ZmSVP protein may be obtained by RNA interference by expression of a gene encoding a micro RNA (miRNA). miRNAs are regulatory agents consisting of about 22 ribonucleotides. miRNA are highly efficient at inhibiting the expression of endogenous genes. See, for example, Javier, et al., (2003) *Nature* 425:257-263, herein incorporated by reference.

For miRNA interference, the expression cassette is designed to express an RNA molecule that is modeled on an endogenous miRNA gene. The miRNA gene encodes an RNA that forms a hairpin structure containing a 22-nucleotide sequence that is complementary to another endogenous gene (target sequence). For suppression of ZmSVP protein expression, the 22-nucleotide sequence is selected from a ZmSVP transcript sequence and contains 22 nucleotides of said ZmSVP protein sequence in sense orientation and 21 nucleotides of a corresponding antisense sequence that is complementary to the sense sequence. miRNA molecules are highly efficient at inhibiting the expression of endogenous genes, and the RNA interference they induce is inherited by subsequent generations of plants.

B. Polypeptide-Based Inhibition of Gene Expression

In one embodiment, the polynucleotide encodes a zinc finger protein that binds to a gene encoding a ZmSVP protein, resulting in reduced expression of the gene. In particular embodiments, the zinc finger protein binds to a regulatory region of a ZmSVP gene. In other embodiments, the zinc finger protein binds to a messenger RNA encoding a ZmSVP protein and prevents its translation. Methods of selecting sites for targeting by zinc finger proteins have been described, for example, in U.S. Pat. No. 6,453,242, and methods for using zinc finger proteins to inhibit the expression of genes in plants are described, for example, in U.S. Patent Publication No. 20030037355; each of which is herein incorporated by reference.

C. Polypeptide-Based Inhibition of Protein Activity

In some embodiments of the invention, the polynucleotide encodes an antibody that binds to at least one ZmSVP protein, and reduces the ZmSVP activity of the ZmSVP protein. In another embodiment, the binding of the antibody results in increased turnover of the antibody-ZmSVP protein complex by cellular quality control mechanisms. The expression of antibodies in plant cells and the inhibition of molecular pathways by expression and binding of antibodies to proteins in plant cells are well known in the art. See, for example, Conrad and Sonnewald (2003) *Nature Biotech.* 21:35-36, incorporated herein by reference.

D. Gene Disruption

In some embodiments of the present invention, the activity of a ZmSVP protein is reduced or eliminated by disrupting the gene encoding the ZmSVP protein. The gene encoding the ZmSVP protein may be disrupted by any method known in the art. For example, in one embodiment, the gene is disrupted by transposon tagging. In another embodiment, the gene is disrupted by mutagenizing the plants of interest using random or targeted mutagenesis, and selecting for plants that have reduced ZmSVP activity.

The invention encompasses additional methods for reducing or eliminating the activity of ZmSVP proteins. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides, and recombinogenic oligonucleobases. Such vectors and methods of use are known in the art. See, for example, U.S. Pat. Nos. 5,565,350; 5,731,181; 5,756,325; 5,760,012; 5,795,972; and 5,871,984; each of which are herein incorporated by reference. See also, WO 98/49350, WO 99/07865, WO 99/25821, and Beetham, et al., (1999) *Proc. Natl. Acad. Sci. USA* 96:8774-8778; each of which is herein incorporated by reference.

In certain embodiments the polynucleotides of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723, 756; 5,593,881; and Geiser, et al., (1986) *Gene* 48:109), lectins (Van Damme, et al., (1994) *Plant Mol. Biol.* 24:825, pentin (described in U.S. Pat. No. 5,981,722), and the like.

The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885, 802; and 5,703,409); barley high lysine (Williamson, et al., (1987) Eur. J. Biochem. 165:99-106; and WO 98/20122) and high methionine proteins (Pedersen, et al., (1986) J. Biol. Chem. 261:6279; Kirihara, et al., (1988) Gene 71:359; and Musumura, et al., (1989) Plant Mol. Biol. 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones, et al., (1994) Science 266:789; Martin, et al., (1993) Science 262:1432; Mindrinos, et al., (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) J. Bacteriol. 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

EXAMPLE 1

Identification and Characterization of a Maize SVP-like MADS-Box Transcription Factor Gene that is Expressed in Ear Meristems Gene expression profiling experiments were conducted to identify genes that are active in the ear meristem of Zea mays when the meristem is producing florets. Ear tip samples from short and long eared maize lines before and after the ear meristem terminates were submitted to Agilent's microarray analysis (Hughes, et al., (2001) Nat Biotechnol. 19:342-7). From these experiments, several ESTs corresponding to a ZmSVP maize gene were identified based on the 60-mer present on the microarray showing the differential signals. The EST that encoded the ZmSVP (designated herein as ZmSVP4) was shown to be the same gene described as ZMM21 in Münster, et al., (2002) Maydica 47:287-301. The ZmSVP nucleotide sequence indicates that this gene encodes a putative SVP-like transcription factor gene based on phylogenetic analysis of Münster, et al., (2002) and our own CLUSTALW alignment with all known arabidopsis MADS-containing ORFs. The ZmSVP gene was expressed in the ear meristem when the meristem was producing spikelets. Using immature ears at various developmental stages before silking, ZmSVP expression was measured using a multiplexed RT-PCR method (U.S. Patent Application Publication No. 2003/0226178) with an internal alpha-tubulin gene control, which did not show changes relative to the levels of total RNA isolated during ear development. The ZmSVP gene was down-regulated to levels below detection in the ear meristem when the meristem was beginning to terminate. The ears were staged by the average number of visible spikelets per row that had formed. During ear development, ZmSVP was expressed at detectable levels until the ears reached approximately between ~5 and ~15 spikelets per row where the expression declined to below detectable levels relative to the alpha-tubulin gene. The short-eared line achieved this decline in ZmSVP expression levels a few days earlier than the long-eared line if both lines are synchronized at the start of spikelet development on the ear. Yet both lines showed this decline at roughly the same stage of ear development as measured by the number of spikelets per row. An investigation of whole plant gene expression revealed low levels of expression in root, stems, and shoot apical/tassel meristems, and developing kernels, most likely everywhere there are meristems. Using RT-PCR at 35 cycles for the ZmSVP gene (by the method described for the CLV3 U.S. Patent Application Publication No. 2003/0226178 but with primers for the ZmSVP4 gene), ZmSVP transcripts were easily detected in all tissues tested except young leaves, which showed lower or below detectable levels of ZmSVP transcripts.

The ZmSVP nucleotide sequence revealed that this gene encodes a putative SVP-like MADS-box transcription factor gene. Although the sequence of a nearly identical ZmSVP maize gene was previously reported and referred to as ZMM21 (Genbank accession number AJ430635; Münster, et al., (2002) Maydica 47:287-301), the expression pattern and function of this maize gene has not been reported. There are, however, reports of the Arabidopsis SVP's role in controlling flowering time (Hartmann, et al., (2000) Plant J. 21:351-60)

and its genetic association with another flowering time control gene FLM (Scortecci, et al., (2003) Plant Mol. Biol. 52:915-22).

The ZmSVP of the present invention is a member of the MIKC-type MADS box genes with MADS (M-), intervening (I-), keratin-like (K-) and C-terminal (C-) domains. See, Münster, et al., (2002) Maydica 47:287-301 and the references cited therein. The MADS box domain functions primarily as DNA-binding but also has been documented as performing dimerizations and accessory factor binding. The I-domain is involved in selective formation of DNA-binding dimers whereas the K-domain is involved in protein-protein interactions, and the variable C-domain is involved in multimeric TF complexes.

Using phylogenetic analyses (i.e., CLUSTALW alignment of amino acid with all MADS box members from *Arabidopsis* then displaying the closest homologs to the AtSVP gene), we determined that ZmSVP4 is a member of the SVP/STMADS11 family of MADS box transcription factors. The SVP/STMADS11 family of MADS box transcription factors is part of a MIKC-type superfamily containing at least four defined domains. The "M" or MADS domain of the ZmSVP4 protein is from amino acids 2 to 60 of SEQ ID NO: 2. Different variants of MADS-boxes exist but all MADS box transcription factors by definition carry this domain. The K-domain of the ZmSVP4 protein covers amino acids 69 to 173 of SEQ ID NO: 2. These two domains are found in most of the MADS box transcription factors. There is a non-conserved "I" domain (the Interval between the "M" and "K" domain) and the nominally conserved C-terminal domain (putatively the activation domain). There appears to be sets of motifs that are common among the AtSVP, the four maize SVP genes and two rice SVP-like genes. These include LRQMRGE(D/E)L at amino acids 108 to 116 (SEQ ID NO: 2) in the K-domain, E(D/E)GQSSES(V/I)(T/M)A at amino acids 192 to 203 and SD(I/V/T)SL(K/R)L(G/S)LP at amino acids 216 to 225 both in the C-domain (C-terminal activation domain).

EXAMPLE 2

Transgenic Maize Plants Expressing ZmSVP Under the Control of the Ubiquitin Promoter Using GS3×HG11 maize plants, transgenic maize plants ($T_0$) were produced that express ZmSVP under the control of the UBI promoter. The transgenic plants comprised stably incorporated in their genomes a polynucleotide construct comprising the following elements in series and in operable linkage: the maize UBI promoter, the 1st intron of UBI, the ZmSVP coding sequence and a portion of the 3' UTR (i.e., nucleotides 42 to 730 of SEQ ID NO: 1), and the PinII terminator. The first phenotype that was noted in the greenhouse-grown $T_0$ transgenic plants was an increase in tassel size, anther density (both similar to TFL phenotype previously described by Shannon and Meeks-Wagner (1991) *Plant Cell* 3:877-892) and glume size on individual anthers (different from TFL phenotype) in all 14 independent transgenic events. In addition, the ears from these plants were somewhat longer than those of non-transgenic lines remaining plant characteristics were not different to non-transgenic lines of the same genotype. $T_1$ seeds for six events were produced and sent to a nursery in Hawaii.

Ears and tassels from segregating $T_1$ plants grown outdoors in Hawaii were analyzed for several phenotypic traits. There was an overall, highly significant 13% increase in spikelets per row (P=0.00036) across all six of the transgenic events and a 20% increase in spikelets per row in the two single copy events, with no significant change in kernel row number as predicted on the basis of our hypothesis that by delaying meristem termination or determinant growth especially in the tassel and ear, or stated in another way, allowing the meristem to remain in an actively functioning or indeterminate state, more cells are generated via cell division from the meristem at the growing points of the plants allowing for more lateral organs and/or larger organ(s) development (i.e., more anthers and ovules for pollination in the tassel and ear, respectively).

Our hypothesis is based in part on the observation that mutations in the SVP gene in *Arabidopsis* were previously shown to hasten transition to flowering (Hartmann, et al., (2000) *Plant J.* 21:351-60). Based on this report, we hypothesized that overexpression of this gene would delay transition to flowering or more specifically transition of the affected meristem from an indeterminate to a determinate state. Therefore, we anticipated that controlling this mechanism in the meristem would be applicable to nearly all plants with active SVP expression.

In addition to the predicted increase in spikelets per row, a 45% increase in the anther density as measured by the number of anthers/cm of the central tassel spike was also observed (P=0.00001). Additionally, the number of tassel branches nearly doubled in transgenics versus non-transgenics (P=0.00006). There were increases in the size of the glumes, occasional tasselseed phenotype and greater incidence of triplet florets in tassels with an extra pedicillate or sessile spikelets.

EXAMPLE 3

Transformation and Regeneration of Transgenic Maize Plants

Immature maize embryos from greenhouse donor plants are bombarded with a plasmid containing the ZmSVP polynucleotide molecule operably linked to a promoter expressible in a plant and the selectable marker gene PAT (Wohlleben, et al., (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the ZmSVP operably linked to the promoter is made. This plasmid DNA plus plasmid DNA containing a BAR selectable marker is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #4 in particle gun #HE34-1 or #HE34-2. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for ZmSVP activity.

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I H$_2$O following adjustment to pH 5.8 with KOH); 2.0 g/l Gelrite (added after bringing to volume with D-I H$_2$O); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H$_2$O following adjustment to pH 5.8 with KOH); 3.0 g/l Gelrite (added after bringing to volume with D-I H$_2$O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_2$O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

EXAMPLE 4

*Agrobacterium*-mediated Transformation of Maize and Regeneration of Transformed Maize Plants For *Agrobacterium*-mediated transformation of maize with a ZmSVP of the present invention polynucleotide molecule operably linked to a promoter expressible in a plant, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the ZmSVP polynucleotide molecule operably linked to the promoter to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

EXAMPLE 5

Variants of ZmSVP

A. Variant Nucleotide Sequences of ZmSVP That Do Not Alter the Encoded Amino Acid Sequence The ZmSVP coding sequence set forth in SEQ ID NO: 3 is used to generate variant nucleotide sequences having the nucleotide sequence of the open reading frame with about 70%, 76%, 81%, 86%, 92% and 97% nucleotide sequence identity when compared to the starting unaltered ORF nucleotide sequence of SEQ ID NO: 3. These functional variants are generated using a standard codon table. While the nucleotide sequence of the variant is altered, the amino acid sequence encoded by the open reading frame does not change.

B. Variant Amino Acid Sequences of ZmSVP

Variant amino acid sequences of ZmSVP are generated. In this example, one amino acid is altered. Specifically, the open reading frame set forth in SEQ ID NO: 1 or 3 is reviewed to determine the appropriate amino acid alteration. The selection of the amino acid to change is made by consulting the protein alignment (with the other orthologs and other gene family members from various species). See, FIG. 1. An amino acid is selected that is deemed not to be under high selection pressure (not highly conserved) and which is rather easily substituted by an amino acid with similar chemical characteristics (i.e., similar functional side-chain). Using the protein alignment set forth in FIG. 1 an appropriate amino acid can be changed. Amino acids that can be varied include, but are not limited to, the following: (1) amino acids in the I-domain and part of the K-domain, particularly amino acids 62-107 of SEQ ID NO: 2 but excluding the conserved amino acids at positions 73 and 76 of SEQ ID NO: 2, and (2) amino acids in part of the C-domain, particularly amino acids 175-190 and 204-215). Once the targeted amino acid is identified, the procedure outlined in Example 5A is followed. Variants having about 70%, 75%, 81%, 86%, 92% and 97% nucleic acid sequence identity to SEQ ID NO: 2 are generated using this method.

C. Additional Variant Amino Acid Sequences of ZmSVP

In this example, artificial protein sequences are created having 82%, 87%, 92% and 97% identity relative to the reference protein sequence. This latter effort requires identifying conserved and variable regions from the alignment set forth in FIG. 1 and then the judicious application of an amino acid substitutions table. These parts will be discussed in more detail below.

Largely, the determination of which amino acid sequences are altered is made based on the conserved regions among SVP4 proteins or among the other related MADS-box containing, SVP-like transcription factors. See FIG. 1. Based on the sequence alignment, the various regions of the SVP4 that can likely be altered are represented in lower case letters, while the conserved regions are represented by capital letters. It is recognized that conservative substitutions can be made in the conserved regions below without altering function. In addition, one of skill will understand that functional variants of the ZmSVP sequence of the invention can have minor non-conserved amino acid alterations in the conserved domain.

ZmSVP belongs to the SVP/STMADS11 family of MADS box transcription factors that is part of a MIKC-type superfamily which contain at least four defined domains. The conserved regions of the ZmSVP4 protein include, for example, the "M" or MADS domain which is from amino acid 2-60 of SEQ ID NO: 2. Different variants of MADS-boxes exist but all MADS box TF by definition carry the M domain. The K-domain covers amino acids 69-173 of SEQ ID NO: 2. These two domains are found in most of the MADS transcription factors. There is a non-conserved "I" domain (the Interval between the "M" and "K" domain) and the nominally conserved C-terminal domain (putatively the activation domain). There appears to be sets of motifs that are common among the AtSVP, the four maize SVP genes and two rice SVP-like genes. These include LRQMRGE(D/E)L at amino acids 108-116 resident in the K-domain, E(D/E)GQSSES(V/I)(T/M)A at amino acids 192-203 and SD(I/V/T)SL(K/R)L(G/S)LP at amino acids 216-225 both in the C-domain (C-terminal activation domain).

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 1.

TABLE 1

| Substitution Table | | | |
|---|---|---|---|
| Amino Acid | Strongly Similar and Optimal Substitution | Rank of Order to Change | Comment |
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |

TABLE 1-continued

| Substitution Table | | | |
|---|---|---|---|
| Amino Acid | Strongly Similar and Optimal Substitution | Rank of Order to Change | Comment |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C, and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involved a 50:50 substitution of the two alternate optimal substitutions.

The variant amino acid sequences are written as output. Perl script is used to calculate the percent identities. Using this procedure, variants of ZmSVP are generating having about 82%, 87%, 92% and 97% amino acid identity to the starting unaltered ORF nucleotide sequence of SEQ ID NO: 2.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. A method for modifying flower development in a plant, said method comprising transforming a plant with a polynucleotide construct comprising a polynucleotide molecule operably linked to a promoter that is expressed in a plant cell, wherein the polynucleotide molecule comprises a nucleotide sequence selected from the group consisting of:
   (a) the nucleotide sequence set forth in SEQ ID NO:1, 3 or 4;
   (b) a nucleotide sequence encoding an amino acid sequence comprising SEQ ID NO:2;
   (c) a nucleotide sequence comprising at least 95% sequence identity to SEQ ID NO:1 or 3, wherein said polynucleotide molecule encodes a polypeptide having ZmSVP activity;
   (d) a nucleotide sequence encoding an amino acid sequence having at least 95% sequence identity to SEQ ID NO:2, wherein said polynucleotide molecule encodes a polypeptide having ZmSVP activity; and
   (e) a nucleotide sequence that is the complement of the nucleotide sequence of (a), (b), (c), or (d);
   and selecting a transformed plant having modified flower development when compared to an untransformed plant.

2. The method of claim 1, wherein relative to an untransformed plant, the transformed plant comprises an increase in the period of time that at least one of its floral meristems is active.

3. The method of claim 1 or 2, wherein relative to an untransformed plant, the transformed plant comprises an increase in the number of florets initiated in an inflorescence.

4. The method of claim 1, wherein said plant is a monocot.

5. The method of claim 4, wherein said monocot is maize, wheat, rice, barley, sorghum, or rye.

6. The method of claim 1, wherein said plant is a dicot.

7. The method of claim 6, wherein the dicot is soybean, *Brassica*, sunflower, cotton, peanut, or alfalfa.

8. The method of claim 1, wherein the plant is maize.

9. The method of claim 8, wherein relative to an untransformed maize plant, the transformed maize plant comprises at least one improvement selected from the group consisting of an increase in floret number per ear, an increase in female floret number per plant, an increase in floret number per tassel, an increase in spiklets per row, an increase in tassel size, an increase in tassel branching, and an increase in anther density.

10. The method of claim 1, wherein the polynucleotide construct is stably incorporated into the genome of the plant.

11. The method of claim 1, wherein the promoter is a flower meristem-preferred promoter or a chemical-regulated promoter.

12. The method of claim 11, wherein the flower meristem-preferred promoter is an ear meristem-preferred promoter or tassel meristem-preferred promoter.

13. A method for modifying reproductive development in a plant, said method comprising transforming a plant with a polynucleotide construct comprising a polynucleotide molecule operably linked to a promoter that is expressed in a plant cell, wherein the polynucleotide molecule comprises a nucleotide sequence selected from the group consisting of:
   (a) the nucleotide sequence set forth in SEQ ID NO:1, 3 or 4;
   (b) a nucleotide sequence encoding an amino acid sequence comprising SEQ ID NO:2;
   (c) a nucleotide sequence comprising at least 95% sequence identity to SEQ ID NO:1 or 3, wherein said polynucleotide molecule encodes a polypeptide having ZmSVP activity;
   (d) a nucleotide sequence encoding an amino acid sequence having at least 95% sequence identity to SEQ ID NO:2, wherein said polynucleotide molecule encodes a polypeptide having ZmSVP activity; and
   (e) a nucleotide sequence that is the complement of the nucleotide sequence of (a), (b), (c), or (d);
   and selecting a transformed plant having modified reproductive development when compared to an untransformed plant.

14. The method of claim 13, wherein relative to an untransformed plant, the transformed plant comprises an increase in the period of time that at least one of its floral meristems is active.

15. The method of claim 13 or 14, wherein relative to an untransformed plant, the transformed plant comprises an increase in the number of florets initiated in an inflorescence.

16. The method of claim 13, wherein the plant is a monocot.

17. The method of claim 16, wherein the monocot is maize, wheat, rice, barley, sorghum, or rye.

18. The method of claim 13, wherein the plant is a dicot.

19. The method of claim 18, wherein the dicot is soybean, *Brassica*, sunflower, cotton, peanut or alfalfa.

20. The method of claim 13, wherein the plant is maize.

21. The method of claim 20, wherein relative to an untransformed maize plant, the transformed maize plant comprises at least one improvement selected from the group consisting of an increase in floret number per ear, an increase in female floret number per plant, an increase in floret number per tassel, an increase in spikelets per row, an increase in tassel size, an increase in tassel branching, an increase in anther density, an increase in the number of kernels per ear, an increase on the number of kernels per plant, and an increase in grain yield.

22. The method of claim 13, wherein the polynucleotide construct is stably incorporated into the genome of the plant.

23. The method of claim 13, wherein the promoter is a flower meristem-preferred promoter or a chemical-regulated promoter.

24. The method of claim 23, wherein the flower meristem-preferred promoter is an ear meristem-preferred promoter or a tassel meristem preferred promoter.

25. A method for increasing the grain yield of a grain plant, said method comprising transforming a plant with a polynucleotide construct comprising a polynucleotide molecule operably linked to a promoter that is expressed in a plant cell, wherein the polynucleotide molecule comprises a nucleotide sequence selected from the group consisting of:
- (a) the nucleotide sequence set forth in SEQ ID NO:1, 3 or 4;
- (b) a nucleotide sequence encoding an amino acid sequence comprising SEQ ID NO:2;
- (c) a nucleotide sequence comprising at least 95% sequence identity to SEQ ID NO:1 or 3, wherein said polynucleotide molecule encodes a polypeptide having ZmSVP activity;
- (d) a nucleotide sequence encoding an amino acid sequence having at least 95% sequence identity to SEQ ID NO:2, wherein said polynucleotide molecule encodes a polypeptide having ZmSVP activity; and
- (e) a nucleotide sequence that is the complement of the nucleotide sequence of (a), (b), (c), or (d);

and selecting a transformed plant having increased grain yield when compared to an untransformed plant.

26. The method of claim 25, wherein the grain plant is selected from the group consisting of maize, wheat, rice, barley, sorghum, and rye.

27. The method of claim 26, wherein the plant is maize.

28. The method of claim 25, wherein the polynucleotide construct is stably incorporated into the genome of the grain plant.

29. The method of claim 25, wherein the promoter is a flower meristem-preferred promoter or a chemical-regulated promoter.

30. The method of claim 29, wherein the flower meristem-preferred promoter is an ear meristem-preferred promoter or a tassel meristem-preferred promoter.

31. The method of claim 25, wherein the increase grain yield occurs when the transformed plants are grown under optimal conditions.

32. A transformed plant comprising a polynucleotide construct comprising a polynucleotide molecule operably linked to a promoter that drives expression in the plant, wherein said polynucleotide molecule comprises a nucleotide sequence selected from the group consisting of:
- (a) the nucleotide sequence set forth in SEQ ID NO: 1, 3 or 4;
- (b) a nucleotide sequence encoding an amino acid sequence comprising SEQ ID NO: 2; and
- (c) a nucleotide sequence that is the complement of the nucleotide sequence of (a) (b).

33. The transformed plant of claim 32, wherein flower development is modified in the transformed plant when compared to an untransformed plant.

34. The transformed plant of claim 32, wherein reproductive development is modified in the transformed plant when compared to an untransformed plant.

35. The transformed plant of claim 32, wherein the plant is a grain plant and the grain yield of the transformed plant is increased when compared to the yield of an untransformed plant.

36. The transformed plant of claim 35, wherein the grain plant is selected from the group consisting of maize, wheat, rice, barley, sorghum, and rye.

37. The transformed plant of claim 32, wherein said plant is a plant cell.

38. The transformed plant of claim 32, wherein said plant is a monocot.

39. The transformed plant of claim 38, wherein said monocot is maize, wheat, rice, barley, sorghum, or rye.

40. The transformed plant of claim 32, wherein said plant is a dicot.

41. The transformed plant of claim 40, wherein the dicot is soybean, *Brassica*, sunflower, cotton or alfalfa.

42. The transformed plant of claim 32, wherein said polynucleotide is stably incorporated into the genome of the plant.

43. The transformed plant of claim 32, wherein the promoter is a flower meristem-preferred promoter or a chemical-regulated promoter.

44. The transformed plant of claim 43, wherein the flower meristem-preferred promoter is an ear meristem-preferred promoter.

45. The transformed plant of claim 32, wherein said plant is a seed.

46. A progeny plant of a transformed plant, said transformed plant comprising a polynucleotide construct comprising a polynucleotide molecule operably linked to a promoter that drives expression in the plant, wherein said polynucleotide molecule comprises a nucleotide sequence selected from the group consisting of:
- (a) the nucleotide sequence set forth in SEQ ID NO: 1, 3 or 4;
- (b) a nucleotide sequence encoding an amino acid sequence comprising SEQ ID NO: 2; and
- (c) a nucleotide sequence that is the complement of the nucleotide sequence of (a) or (b);

wherein the progeny plant comprises the polynucleotide construct.

47. A transformed plant cell comprising a polynucleotide construct comprising a polynucleotide molecule operably linked to a promoter that drives expression in the plant, wherein said polynucleotide molecule comprises a nucleotide sequence selected from the group consisting of:
- (a) the nucleotide sequence set forth in SEQ ID NO: 1, 3 or 4;
- (b) a nucleotide sequence encoding an amino acid sequence comprising SEQ ID NO: 2; and
- (c) a nucleotide sequence that is the complement of the nucleotide sequence of (a) (b).

48. An isolated polynucleotide molecule comprising a nucleotide sequence selected from the group consisting of:
- (a) the nucleotide sequence set forth in SEQ ID NO: 1, 3 or 4;
- (b) a nucleotide sequence encoding an amino acid sequence comprising SEQ ID NO: 2; and
- (c) a nucleotide sequence that is the complement of the nucleotide sequence of (a) or (b).

49. An expression cassette comprising a polynucleotide molecule, said polynucleotide molecule comprising a nucleotide seguence selected from the group consisting of:
- (a) the nucleotide sequence set forth in SEQ ID NO: 1, 3 or 4;
- (b) a nucleotide sequence encoding an amino acid sequence comprising SEQ ID NO: 2; and
- (c) a nucleotide sequence that is the complement of the nucleotide sequence of (a) or (b).

50. The expression cassette of claim 49, wherein said polynucleotide molecule is operably linked to a promoter that drives expression in a plant.

* * * * *

UNITED STATES PATENT AND TRADEMARK OFFICE
CERTIFICATE OF CORRECTION

PATENT NO. : 7,803,998 B2
APPLICATION NO. : 11/612518
DATED : September 28, 2010
INVENTOR(S) : Bruce et al.

It is certified that error appears in the above-identified patent and that said Letters Patent is hereby corrected as shown below:

Column 64, Claim 49, line 52, "seguence" should read --sequence--.

Signed and Sealed this
Second Day of August, 2011

David J. Kappos
*Director of the United States Patent and Trademark Office*

SEQUENCE LISTING

```
<160> NUMBER OF SEQ ID NOS: 11

<210> SEQ ID NO 1
<211> LENGTH: 1041
<212> TYPE: DNA
```

<213> ORGANISM: Zea mays
<220> FEATURE:
<221> NAME/KEY: CDS
<222> LOCATION: (47)...(721)

<400> SEQUENCE: 1

```
tcgtgggcgt aggacgagag agaggatcgg cggcggcgtg tgggag atg gcg cgc        55
                                                    Met Ala Arg
                                                    1 gag agg cgg gag ata cgg cgg ata gag agc gcg gcg gcg cgg cag gtg       103
Glu Arg Arg Glu Ile Arg Arg Ile Glu Ser Ala Ala Ala Arg Gln Val
    5                  10                  15 acc ttc tcc aag cgc cgg cgc ggg ctg ttc aag aag gcg gag gag ctc       151
Thr Phe Ser Lys Arg Arg Arg Gly Leu Phe Lys Lys Ala Glu Glu Leu
 20                  25                  30                  35 gcc gtg ctg tgc gac gcc gac gtc gcg ctc gtc gtg ttc tcc gcc acc       199
Ala Val Leu Cys Asp Ala Asp Val Ala Leu Val Val Phe Ser Ala Thr
                 40                  45                  50 ggc agg ctc tcg cag ttc gcg agc tcc agt gtg aat gac atc gtt gac       247
Gly Arg Leu Ser Gln Phe Ala Ser Ser Ser Val Asn Asp Ile Val Asp
             55                  60                  65 aag tac agt aca cat tct aag aat ctg ggg aaa tca cat cag cag cct       295
Lys Tyr Ser Thr His Ser Lys Asn Leu Gly Lys Ser His Gln Gln Pro
         70                  75                  80 tct att gat ttg aat gta gag cag agc aaa tac agc ggc ttg aac gag       343
Ser Ile Asp Leu Asn Val Glu Gln Ser Lys Tyr Ser Gly Leu Asn Glu
     85                  90                  95 caa ctt gct gaa gaa act aat gga ctt aga cag atg aga ggt gaa gac       391
Gln Leu Ala Glu Glu Thr Asn Gly Leu Arg Gln Met Arg Gly Glu Asp
100                 105                 110                 115 ctt gag gga ttg agt gta gag gaa ttg cac cga atg gaa agg aaa ctt       439
Leu Glu Gly Leu Ser Val Glu Glu Leu His Arg Met Glu Arg Lys Leu
                 120                 125                 130 gaa gca gga ctg cat aga gtg att agt aca aag gac cag cta ttc atg       487
Glu Ala Gly Leu His Arg Val Ile Ser Thr Lys Asp Gln Leu Phe Met
             135                 140                 145 caa caa atc ggc gaa tta ctg caa aag ggc aca cag cta gaa gat gag       535
Gln Gln Ile Gly Glu Leu Leu Gln Lys Gly Thr Gln Leu Glu Asp Glu
         150                 155                 160 aac agg cgt cta aaa gaa caa atg ccc cag gtg cta acg ggt ggc aca       583
Asn Arg Arg Leu Lys Glu Gln Met Pro Gln Val Leu Thr Gly Gly Thr
     165                 170                 175 atg gtg gtt gct gct gct gca gaa aat atc ctc act gaa gac ggg cag       631
Met Val Val Ala Ala Ala Ala Glu Asn Ile Leu Thr Glu Asp Gly Gln
180                 185                 190                 195 tcg tct gaa tct gta atg act gca ttg cat tca gga agc tcg ctc gac       679
Ser Ser Glu Ser Val Met Thr Ala Leu His Ser Gly Ser Ser Leu Asp
                 200                 205                 210 tgt gat gat ggt tcc gat ata tcc ttg aag ttg tcg ttg cct                721
Cys Asp Asp Gly Ser Asp Ile Ser Leu Lys Leu Ser Leu Pro
             215                 220                 225 tgaaaggaag gaccatcgca tcgcatgtta tctgcatgag tggggctgac accagtgctt      781
ctaagaagac aaagactggg atagtcccat tcgcggcatt atattggttt aaccagatgt      841
gctgtccttg tgcatgtctg tacttcaaag tggctaacgc gaaatttgta tatataatag      901
tgtatgcgct gcgttatctt cgttctaaaa atctgtattg tttcgttgct ggtgctatat      961
ttgttggtct attatatata tgcacttaac tgttatctct attctattaa gaacataata     1021
tagacacatg atgctaaaaa                                                 1041
```

<210> SEQ ID NO 2
<211> LENGTH: 225
<212> TYPE: PRT
<213> ORGANISM: Zea mays

<400> SEQUENCE: 2

```
Met Ala Arg Glu Arg Glu Ile Arg Arg Ile Glu Ser Ala Ala Ala
1               5                   10                  15

Arg Gln Val Thr Phe Ser Lys Arg Arg Gly Leu Phe Lys Lys Ala
            20                  25                  30

Glu Glu Leu Ala Val Leu Cys Asp Ala Asp Val Ala Leu Val Val Phe
            35                  40                  45

Ser Ala Thr Gly Arg Leu Ser Gln Phe Ala Ser Ser Ser Val Asn Asp
    50                  55                  60

Ile Val Asp Lys Tyr Ser Thr His Ser Lys Asn Leu Gly Lys Ser His
65                  70                  75                  80

Gln Gln Pro Ser Ile Asp Leu Asn Val Glu Ser Lys Tyr Ser Gly
                85                  90                  95

Leu Asn Glu Gln Leu Ala Glu Glu Thr Asn Gly Leu Arg Gln Met Arg
                100                 105                 110

Gly Glu Asp Leu Glu Gly Leu Ser Val Glu Glu Leu His Arg Met Glu
            115                 120                 125

Arg Lys Leu Glu Ala Gly Leu His Arg Val Ile Ser Thr Lys Asp Gln
        130                 135                 140

Leu Phe Met Gln Gln Ile Gly Glu Leu Leu Gln Lys Gly Thr Gln Leu
145                 150                 155                 160

Glu Asp Glu Asn Arg Arg Leu Lys Glu Gln Met Pro Gln Val Leu Thr
                165                 170                 175

Gly Gly Thr Met Val Val Ala Ala Ala Glu Asn Ile Leu Thr Glu
            180                 185                 190

Asp Gly Gln Ser Ser Glu Ser Val Met Thr Ala Leu His Ser Gly Ser
            195                 200                 205

Ser Leu Asp Cys Asp Asp Gly Ser Asp Ile Ser Leu Lys Leu Ser Leu
        210                 215                 220

Pro
225
```

<210> SEQ ID NO 3
<211> LENGTH: 675
<212> TYPE: DNA
<213> ORGANISM: Zea mays

<400> SEQUENCE: 3

```
atggcgcgcg agaggcggga gatacggcgg atagagagcg cggcggcgcg gcaggtgacc      60
ttctccaagc gccggcgcgg gctgttcaag aaggcgagg agctcgccgt gctgtgcgac     120
gccgacgtcg cgctcgtcgt gttctccgcc accggcaggc tctcgcagtt cgcgagctcc     180
agtgtgaatg acatcgttga caagtacagt acacattcta agaatctggg aaatcacat     240 cagcagcctt ctattgattt gaatgtagag cagagcaaat acagcggctt gaacgagcaa     300
cttgctgaag aaactaatgg acttagacag atgagaggtg aagaccttga gggattgagt     360
gtagaggaat tgcaccgaat ggaaaggaaa cttgaagcag gactgcatag agtgattagt     420
acaaaggacc agctattcat gcaacaaatc ggcgaattac tgcaaaaggg cacacagcta     480
gaagatgaga acaggcgtct aaaagaacaa atgccccagg tgctaacggg tggcacaatg     540
```

```
gtggttgctg ctgctgcaga aaatatcctc actgaagacg ggcagtcgtc tgaatctgta    600
atgactgcat tgcattcagg aagctcgctc gactgtgatg atggttccga tatatccttg    660
aagttgtcgt tgcct                                                     675

<210> SEQ ID NO 4
<211> LENGTH: 10615
<212> TYPE: DNA
<213> ORGANISM: Zea mays
<220> FEATURE:
<221> NAME/KEY: intron
<222> LOCATION: 229 - 4137, 4220 - 4932,  4995 - 5080, 5181 - 5270,
      5313 - 9782, 9825 - 9933,10092 - 10286
<223> OTHER INFORMATION: 229 - 4137
<220> FEATURE:
<221> NAME/KEY: exon
<222> LOCATION: 1 - 228, 4138 - 4219, 4933 - 4994, 5081 - 5180,
      5271 - 5312, 9783 - 9824, 9934 - 10091, 10287 - 10615

<400> SEQUENCE: 4
tcgtgggcgt aggacgagag agaggatcgg cggcggcgtg tgggagatgg cgcgcgagag     60
gcgggagata cggcggatag agagcgcggc ggcgcggcag gtgaccttct ccaagcgccg    120
gcgcgggctg ttcaagaagg cggaggagct cgccgtgctg tgcgacgccg acgtcgcgct    180
cgtcgtgttc tccgccaccg gcaggctctc gcagttcgcg agctccaggc acgcactctc    240
gatcgatcga tcactccgct agctagccta gctacatacc ctaccgtgtt gctcagctcc    300
atccgcgaca cgcccatccg acgtcacatc acatctgccg ccgttcttcg aacccttttt    360 tttccttat cgccacgcat ggcgtgtgtt ttctcgtttg aaattgggat ctggatcttc    420
ttttggcacg gtggcttggt gtttcggatc cttgcactag ggtttcgtgc ttggccatac    480
tacaaattct ctctctctct ctcctttcct agggtttggt tttcatttgg aagacaatat    540
gctgagcgaa ttcgttttct gtttgaatac ggtagaactt gttgtatgaa cggaaatcga    600
gcttcccttg aacatctagc gcctttgttg tgcgtgtgcc tattcccgcc agctccccgg    660
ctagcttctc agagaaatgg ggaattttct acagtatttc cctggttttc tacagtgctt    720
cccgtcagct cgcggattac tcttttttacg gtgggccgaa tcgctgtagc tcgctgccga    780
gagcactccg gccggtgtac gcccgctaat tttctgcccg tcgcttgtca aacgctgctg    840
ctgatggact cgatcaaaca ctgtggatca gcgcgtggcg gtcgttgata agctgagagc    900
tcatgtcgaa cggccgtacc tgtgatttta tgtgccggtt ttggttcatg catgcacgga    960
cttgatcgtt ctccctcccc ggctgctgaa gcctttcgtg attcgtgctg ctgggataaa   1020
ctattctggt caagtaccgc tgcttgtggt gctggcgctg catctggttt tcgtgattcg   1080
tgcatgtttg atgacgggcg tttcaccatt tttctttgtg gagcacacat gcatggcttg   1140
ttccgtgcca atcgaagtac ataagcagaa catttgtatg caaagtagtg tgtgtttagt   1200
tcagtttttt ttataaatct gtttctattt taaaaaagca gaagctgaat caaaggggtt   1260
tatcttttct gcctctacta tggaaaatca gttttttttaa tacgaatttt aaggaactta   1320
tactctgctt ttttgctgct tatccaagtt cgatatatta ataaagagtt taaacaagca   1380
attaaaacga gattcaaaat aattatgtgt tataataaat aaaaaaatta ttaataaaaa   1440
tattagaatg ggattgtaaa attgattat taattcaata tattaatgag gagatagagt   1500
aaataggaaa taaatggaa ttaaaaataa ttaagtgtta gaataagtaa aataaatata   1560
tatattatta aaaaaatata gcaagtggag tctagttttta ttagtaaaaa tattaggaac   1620
ccaaatgtga aattatttt taattagata tatcgattag gatatatagt taaataaagt   1680
```

```
gcatataaat agtatataat ttgtttacag tagacaatcc atagtaattt gaatcaaacg    1740
acttacacca atttttttat agtggacagc tcatagcaaa ttttttacag ctcactagga    1800
tgtttctcta ttcttcctag agcatatgcc tgtaatcatg ctagagtgct acttatttta    1860
ttgataaatt caatatgata gtaagaggtt atttcattat tatttttga atattataca     1920 tgcacaaaca taactcatcc tcaaaagtga gtccttttgg ttattcatta tatttgatat    1980
gtataacggc catttcatta actcacaatt atttagaatc ttttgcttgc ccgatttagt    2040
gttgtttcta cgaacccaca ttttacacag agactacact accggaaaca actgctttgt    2100
cgagtgataa acaatcgaga aactcttttgc cgagtgtgac tttcgtcaaa aaagtctcgg    2160
cgaattgtac atcgccagcg acttctttgc tgagtattt ttgtctggca ctcggcaaag     2220
actctcggcg aaaaaacaa aaatatactt tgtcgagtgt cagaaaaagg cactcgacga     2280
ataattaatt tgttgagtgt cttctagagg acactcgaca aaaaagttat tttgccgagt    2340
gtcaactccg gacactcggc ataagtaaca atcatcaact atagacggtt gctgatggcc    2400
atttgccgtg cgtctcattt cgtcgagagc ttggcactcg gtaaagactg ctttgctaag    2460
cgtcggtgtc tgccgagtgt ttcacgcttg tcaaaggagg tctgtgtcga gtgtcattat    2520
tcgtcgagag tggcactcgg caaatcttat tacactcaac aaagttcctg acactcggca    2580
aagagcttgt ttctggtagt gctagtagac aagtgaataa aatgttagag caacttaaga    2640
gactctttat atcattctcg gttatagaa attgagattt tgctgaaaaa gtactctcta     2700
gcagcgtttt taactgaatc tccaaatata gacatcctct attctagatt tttcgctagc    2760
caaagatgga gaatacatat ggctcactag agttcacaca agatatagaa aacttattgt    2820
tgggtagaaa gatgtataaa aggaatatac tcaaattgct ttctaaataa taacttattg    2880
ttgggtagaa aaaatgttga aaaactcttc gagatgccct tagttaacag gataagcata    2940
tgtttgaagt ttatctgtat gcctcgattt ttgctagtgt ggatggcata taataagata    3000
tgttggtgag tacactgtgc ataaatctct atgatccggt tcagtttcat ggtcccgttg    3060
gagcttgtgg ctttagaaac actgcaagaa ctgcacgttc aatggagggg caccatgagt    3120
ttaggttgtt ctatgggagt tcatgagcct agggacggag ccagaaaaca gtttagcagt    3180
gaattaaacc gctacattga tataatctta ctaaatcact cactatagac ataaatata     3240 taataagatt atactatgtt ttaggagaga ctttagtgga ctcaatagct tagtgaccaa    3300
gtttctggat tgatggaatc gaggaacaga aacatggtac gcggtataat actaaaacta    3360
tgaaaacgag attgtttcca cggaacgaac attcgcgaaa cgagaaacct ggccaagtct    3420
ttagttcccg gtttcttatc tgcatagaca ccggagcggt gggaggctgg agtcccaccg    3480
ctggatccgt gcctgcatgg gtctaacctt gcaagtaaca ggcgcgaagg ggctcagcca    3540
ttcattgggc cgctataaca taatgcttgt tcgaggttgg tcatttttt cagtttctgt     3600 tgcacatttg ccttgctaac ttaccttttgg gtccctgtat gtatgggtga tctcccccctt    3660 aggaaaatct tatactcgat tcatttttct tttaatacaa agacttgtat atctcttgtg    3720
tgtttgagtg aaaagctata tgttatgtga tttaatctca ttttctagct gttctacctt    3780
atctctttct ttacattgat aattaataca tgcatgtcac ttgatccata catttccata    3840
tccaacactg tatgtgactt atagtaatct aaaagactag acagatgcca ctactatgac    3900
accacaaatg cctctgcata gtactaacgt tagatctggt tgcaaacatg gaatgttttt    3960
ctcaattcct actggaacct aatttttcc tattaaattt ctgcatttca ctctgacaac     4020
tgaagatgct gacatttcta tattgctgtg ttttcaaatt tcatatcctc attgccattg    4080
```

```
taagcttcca ttatatgttt tcattattta ccgtttgctt ttgcttttga gctccagtgt    4140
gaatgacatc gttgacaagt acagtacaca ttctaagaat ctggggaaat cacatcagca    4200
gccttctatt gatttgaatg tatgttatgt tagcaatatt tttccttttt tctttccttg    4260
aacttttctt actaataggc aatagtgtaa agcacttttta caggaaagac agatgttaaa    4320
agttagaaat gtgtgggaag tctagtcggt ccacagacag caattacatt tttgttgtgc    4380
aaacaattta atatgaacta cttttttcgta gttccttgtg attaagtcat gcttctgtgg    4440
acagttctta gctgatgcaa actttcatag ctcttagtat aaactattat agatcagagt    4500
acaagaacat tggaaggcat actcaaataa ggggatatac attgaataaa gattgcaaag    4560
tagtcttttc tgattgatta attattcttg agcaatatta ttagtgtcta cacttacttt    4620
tatataacta tatgtagaaa aatcgatgtt taccttctga acagaaggaa ttgactggta    4680
aatttatcaa gctatccttt ttttccttca atgtgatatg tcaagataca ccttggtgaa    4740
atgaataatt gtttatccat agtaccacat agtattcctt acaatcttag tgttaatcag    4800
tcttggactt cttatcctcc aagtgtagtt tgcatgcaca ctactgtttg gagaattaca    4860
gtatgtgtat acgtatattt aatgtttcat ttaacttata tactaatcct attttcccctt    4920 ataatttttc aggtagagca gagcaaatac agcggcttga acgagcaact tgctgaagaa    4980
actaatggac ttaggttatg ttttgtttca tacacaatga ttatgtgatt caagaacat    5040 ttgtttcata cacaaatgac tttactgttc gataatgtag acagatgaga ggtgaagacc    5100
ttgagggatt gagtgtagag gaattgcacc gaatggaaag gaaacttgaa gcaggactgc    5160
atagagtgat tagtacaaag gtagggtgac tgctcaacga gtcctacatc cttcagattc    5220
tcgtttgagt ttgtgcttaa ctatttctca tacaatggat atctcttcag gaccagctat    5280
tcatgcaaca aatcggcgaa ttactgcaaa aggtgagaaa tgattatata atatgtagta    5340
gcaaactagt ggcgttaact gcaaaatgac atttttaatt aagttcctta tttgagatcc    5400
tgccatttca ttagtatgtt atatgtttac atggaattta tatcaaaatc gaacgaagtt    5460
gcaagaatct tggaaagtat gccacccatt cccaggccca tgcatgggat agaaatagaa    5520
tgcagtttca aaagataaac gatctcgcgt caatttcctt ttctcatact ttattcggaa    5580
aatctcatct agattttacg tgttcaaatt ttaaccaaga tcctaaaatg atggcttagc    5640
tggttattct ggtgatcagc ttagattatc ccatatgttc caagcgtgac ctcagttgga    5700
cgagctgatc atttctagtg gaaccacaca aagaggattg gtaacaactg aattagtaga    5760
aaagagtaga tcgaaaagag agatgcttgc tagctagata ggatatgcat atatagcact    5820
catgatatgg gccaatgaaa gttgtagaat tgaattcagt tgatatgggt ggtaggtcat    5880
gtgccagtct cttaagaatg ggtagcacag tttgttaaga aaacactttg accactatgg    5940
agaagccctc tgggcattaa cttttagaaa gttttcttca acacgacagg caagaggaga    6000 ccccaaaca caaaccgata taactcgcaa gaagctgggg atatcatggt ttatagacgc    6060
atacataaaa agggagcaaa taatgtgtg ccaaccgttt tctgttgtta ctgtgcttag    6120
caccagggac ttgctaaaat tttggtacct gaaatctaga caacggttag aattgtattt    6180
ttttggaata ttgggcttat tatctagcat ttcattaaaa taagggagat gctaacgaag    6240
tttacatctt acatggatga gaggcgctcc ctcctttagg ctatcttgag tagatccctt    6300
atcacatcct ctattttata tcatatttca agcttactct gtaaacagtg tcatcatcta    6360
cagttccgcg gcccctattt catcctgtct actggacaca gtcttaggcg gcgctatcgc    6420
```

```
ggattagggc tagtttagaa ggaatggatt ggcgaaaggg cctctagctg agttggttag    6480
gtggtctgag tagcactcct caggtcctag gttcgactcc ccgtgggagc gaatttcagg    6540
ctgtggttaa aaaaatcccc tcgtctgtcc cacgccaaag cacaggtcta aggctcagcc    6600
ccggtcgtgg tcgttctcac atgggcttcg atgccgatgt gtatggtggg ggcaggggtt    6660
cgggggtttt cttgacctgt gtgagaaggt cttcttctta atacaatacc tgggggctgt    6720 cttaccccccg caggtcaagt ttttttttttt agaaggaatg gattgaaaag gtctaaaatt    6780
ctgttgctgt taacaaatga ataataaaga gattttagcc tcttcaatct gctctaattt    6840
acttgctctc aaacacactc ttgaggcttt gtttagttgc attaaattcc tttatattca    6900
actttgacta ggaataggaa gagatttaat taatccccctt caattttctt aaccgaacat    6960
gccctaaggt gtccattaat tactcattac attttgggca atcaataggg gtgtagcacc    7020
ccccccccca aaaaaatac caggtagagt attcatctct aactttggag aaagccgctt    7080
gggtcgattt gagattgcta tcggttgtac taaaagttgc agtaccaacc ttgtagttaa    7140
agttttttta ttcgaggttg tttggtcgtc caaatatgcg tcacaagatt ttataaagtt    7200
aatactaaaa taatctgtat tgtatagtcg tcacaagtat gtaatggtag caaacaatta    7260
ggcgggatgc atgagaaaca accaaaacaa aattatagat ctctaaaagt tatataactt    7320
tgtatttcac ataaaaaatt atctaaagtc gttttaatga caaaatatttt taagcttgtg    7380 tttctttgtc gtcttcagaa aatagtgaac gttatcaata tatcctttag agcgtcaatg    7440
catgtttttt ttacgaaggg gcgaagcccc ctatttcatt aagaaatagg caagtttgaa    7500
acaaccgcgc accacgcggt aaaacctcca aaagaccaac cacggccagc accctatcta    7560
gactctaacc actatcacga gatcagtgaa gagcctacga taacaggaaa agttttggcc    7620
tacgaaggac tacataagac tttcttattt acatcccaac aagacagaca gaggcctcaa    7680
aatgaactga acagtctaga cagcaaaaga cagacaacta tccaaatcaa cttcccagtt    7740
ccagcttcgt atcattcaga aatacgcctg tcgagagggc accaccccga ggcccttccg    7800
aaagcttcac ttgccgtctt tcggattaac ttgcttccta gcaccaccat tctttgctcc    7860
ttctttttct gacgaatcgc ccaagaatcc aaccagaaga ggcaaagaaa aatgatgtta    7920
gacggatcaa gtaaatgatt ttttccaaag caccaatcat ttctagtgcg ccaaatagcc    7980
cagaataaag caccgcaacc aaataacaca agatgagcaa tcttgtcttt tggtttacaa    8040
aaccaattgt catacatatc tttgatattt ttcgggattg atctcaaatt caaagcaact    8100
tgaataactc tccacatata ttgagcaatg gggcatttaa agaacaggtg atcaatagat    8160
tcatccaccc cacagaagca gcagtttaaa gaaccaaacc agcacctttt cttcaggtta    8220
tccttagtaa gaatcttatt tcttaccact aaccagaaga ataccttgat tttatgaggc    8280
aatttagatt tccacaaaaa cttatatgga atcaaaattt gatttttccat tttctttctg    8340 tacaaagaat taactgagaa gccttttttcc ccagagtcca cacaattttta tcatcatgat    8400 cagatagact tacctgatta caataattaa tcaattcatc aaaaagcaac ctcaaattac    8460
ccacaatcct tcttctgaaa gtaagagact caaatttaga tgtgaaaacc tctttaacag    8520
aaacatcttt atcataggtc aagtcaaaaa gaacaggaaa ctggatagac aatggttggt    8580
tacccaacca agtgctttttc cagaaactag tattcaaacc attgccaact tcagttttac    8640
aatatttgta aaagatgtct cgtaaactca ggagtttttt tccagaaatg agagtcattt    8700 tgttttttgct taaccaaaat aagggggtttt cccttaatgt acttactagc aataatcttt    8760
tgccataagc cattcgaatt cttaatattc cacagccatt tagaaagtaa ggaatcattc    8820
```

-continued

```
ataacttcaa gatttaaaac acccaaacca ccctgatttt tgggagagca cactgacacc      8880
caatcagcta aatgaaattt tttggactgc tttccccct gccaagaag cctccttctc        8940
aacaaatcaa ttttttttga taacagtctt aggggcagga tagatcgaaa gcatatataa     9000
aggaacatta gaaagacaac tatttagcag agtaagtcta ccacccagat tcaggaatct     9060
accctaagcg tcaatgcatg ttgtatattc attcacggtt catctgcatt atttatataa     9120
aaccttattg ttgatgcaat cttttgtaaa catatgatac aatcaacgat aaattaagaa     9180
atctaaacaa aaagataacc attgcaacta taccatatga gaggatgaac gtgctaacct     9240
taattaagtg aaatattcaa caaattcttc aaaaaaaatg tacaacacat cctctcttat     9300
agagtattat tttaccttca tacatagtac acaatatatc agaggattaa ctcacacaaa     9360
cgaagaaata ttacacacca accctcaaac ttatgtagcc aatgaacaaa actcaaatct     9420
gatttgctac tgatttctat tacattcaaa catatcgact tgctacttttt cctatcctat   9480
aaattatata aatcaaccac aaatatcaag aaatctaaac aaagaataac tacttcaact     9540
ctactatatg agagattgaa cttgttaacc tttttcaca cttaaatgag agaaatcttc      9600
aacggattct tcgaaaagat tggacaacat ctcccctctt ttttcatcag cttatggtga    9660
cacatgaata aagagttcca tgttccatat ttcatgaaga cgtcgaacat gcatctacaa    9720
atacatttaa attgaatgga cgctttaatc atgcaatctt tttatccgaa ttactgcaaa    9780
agggcacaca gctagaagat gagaacaggc gtctaaaaga acaagtaaca gaccgtatat    9840
atatttctct atatatgtag tgccaggact tcggttgtaa caaaccgtat aatgaagagc    9900
acgtttataa ttccttattc tttatataag cagatgcccc aggtgctaac gggtggcaca    9960
atggtggttg ctgctgctgc agaaaatatc ctcactgaag acgggcagtc gtctgaatct    10020
gtaatgactg cattgcattc aggaagctcg ctcgactgtg atgatggttc cgatatatcc    10080
ttgaagttgt cgtgagtgca ctccaaaaca tttatgctta atttgttgca tgagcaatta    10140
tgaaacactt atgctttgaa gttaataata atatatgcct ggaagctaag tagaaagatt    10200
ttcatgaaaa attaaatcgt gcatggtttt ctttgtaccc attagattct taaatccaaa    10260
ggactatgaa ctctttgacc atgcaggttg ccttgaaagg aaggaccatc gcatcgcatg    10320
ttatctgcat gagtggggct gacaccagtg cttctaagaa gacaaagact gggatagtcc    10380
cattcgcggc attatattgg tttaaccaga tgtgctgtcc ttgtgcatgt ctgtacttca    10440
aagtggctaa cgcgaaattt gtatatataa tagtgtatgc gctgcgttat cttcgttcta    10500
aaaatctgta ttgtttcgtt gctggtgcta tatttgttgg tctattatat atatgcactt    10560
aactgttatc tctattctat taagaacata atatagacac atgatgctaa aaaaa         10615
```

<210> SEQ ID NO 5
<211> LENGTH: 240
<212> TYPE: PRT
<213> ORGANISM: Arabidopsis thaliana

<400> SEQUENCE: 5

```
Met Ala Arg Glu Lys Ile Gln Ile Arg Lys Ile Asp Asn Ala Thr Ala
  1               5                  10                  15

Arg Gln Val Thr Phe Ser Lys Arg Arg Arg Gly Leu Phe Lys Lys Ala
             20                  25                  30

Glu Glu Leu Ser Val Leu Cys Asp Ala Asp Val Ala Leu Ile Ile Phe
         35                  40                  45

Ser Ser Thr Gly Lys Leu Phe Glu Phe Cys Ser Ser Ser Met Lys Glu
```

```
                50                  55                  60
Val Leu Glu Arg His Asn Leu Gln Ser Lys Asn Leu Glu Lys Leu Asp
 65                  70                  75                  80

Gln Pro Ser Leu Glu Leu Gln Leu Val Glu Asn Ser Asp His Ala Arg
                 85                  90                  95

Met Ser Lys Glu Ile Ala Asp Lys Ser His Arg Leu Arg Gln Met Arg
            100                 105                 110

Gly Glu Glu Leu Gln Gly Leu Asp Ile Glu Glu Leu Gln Gln Leu Glu
        115                 120                 125

Lys Ala Leu Glu Thr Gly Leu Thr Arg Val Ile Glu Thr Lys Ser Asp
130                 135                 140

Lys Ile Met Ser Glu Ile Ser Glu Leu Gln Lys Lys Gly Met Gln Leu
145                 150                 155                 160

Met Asp Glu Asn Lys Arg Leu Arg Gln Gln Gly Thr Gln Leu Thr Glu
                165                 170                 175

Glu Asn Glu Arg Leu Gly Met Gln Ile Cys Asn Asn Val His Ala His
            180                 185                 190

Gly Gly Ala Glu Ser Glu Asn Ala Ala Val Tyr Glu Glu Gly Gln Ser
        195                 200                 205

Ser Glu Ser Ile Thr Asn Ala Gly Asn Ser Thr Gly Ala Pro Val Asp
    210                 215                 220

Ser Glu Ser Ser Asp Thr Ser Leu Arg Leu Gly Leu Pro Tyr Gly Gly
225                 230                 235                 240

<210> SEQ ID NO 6
<211> LENGTH: 163
<212> TYPE: PRT
<213> ORGANISM: Oryzsa sativa

<400> SEQUENCE: 6

Asp Lys Tyr Asn Thr His Ser Asn Asn Leu Gly Lys Ala Glu Gln Pro
 1               5                  10                  15

Ser Leu Asp Leu Asn Leu Glu His Ser Lys Tyr Ala His Leu Asn Glu
                20                  25                  30

Gln Leu Ala Glu Ala Ser Leu Arg Leu Arg Gln Met Arg Gly Glu Glu
            35                  40                  45

Leu Glu Gly Leu Ser Ile Asp Glu Leu Gln Gln Leu Glu Lys Asn Leu
        50                  55                  60

Glu Ala Gly Leu His Arg Val Met Leu Thr Lys Asp Gln Gln Phe Met
 65                  70                  75                  80

Glu Gln Ile Ser Glu Leu Gln Arg Lys Ser Ser Gln Leu Ala Glu Glu
                 85                  90                  95

Asn Met Gln Leu Arg Asn Gln Val Ser Gln Ile Ser Pro Ala Glu Lys
            100                 105                 110

Gln Val Val Asp Thr Glu Asn Phe Val Thr Glu Gly Gln Ser Ser
        115                 120                 125

Glu Ser Val Met Thr Ala Leu His Ser Gly Ser Ser Gln Ser Gln Asp
130                 135                 140

Asn Asp Asp Gly Ser Asp Val Ser Leu Lys Leu Gly Leu Pro Cys Gly
145                 150                 155                 160

Ala Trp Lys

<210> SEQ ID NO 7
<211> LENGTH: 223
<212> TYPE: PRT
```

<213> ORGANISM: Oryza sativa

<400> SEQUENCE: 7

```
Met Ala Arg Glu Arg Glu Ile Arg Arg Ile Glu Ser Ala Ala Ala
 1               5                  10                  15

Arg Gln Val Thr Phe Ser Lys Arg Arg Gly Leu Phe Lys Lys Ala
                20                  25                  30

Glu Glu Leu Ala Val Leu Cys Asp Ala Asp Val Ala Leu Val Val Phe
                35                  40                  45

Ser Ser Thr Gly Lys Leu Ser Gln Phe Ala Ser Ser Asn Met Asn Glu
                50                  55                  60

Ile Ile Asp Lys Tyr Thr Thr His Ser Lys Asn Leu Gly Lys Thr Asp
 65                  70                  75                  80

Lys Gln Pro Ser Ile Asp Leu Asn Leu Glu His Ser Lys Cys Ser Ser
                85                  90                  95

Leu Asn Glu Gln Leu Ala Glu Ala Ser Leu Gln Leu Arg Gln Met Arg
                100                 105                 110

Gly Glu Glu Leu Glu Gly Leu Ser Val Glu Glu Leu Gln Gln Met Glu
                115                 120                 125

Lys Asn Leu Glu Ala Gly Leu Gln Arg Val Leu Cys Thr Lys Asp Gln
                130                 135                 140

Gln Phe Met Gln Glu Ile Ser Glu Leu Gln Arg Lys Gly Ile Gln Leu
145                 150                 155                 160

Ala Glu Glu Asn Met Arg Leu Arg Asp Gln Met Pro Gln Val Pro Thr
                165                 170                 175

Ala Gly Leu Ala Val Pro Asp Thr Glu Asn Val Leu Thr Glu Asp Gly
                180                 185                 190

Gln Ser Ser Glu Ser Val Met Thr Ala Leu Asn Ser Gly Ser Ser Gln
                195                 200                 205

Asp Asn Asp Asp Gly Ser Asp Ile Ser Leu Lys Leu Gly Leu Pro
                210                 215                 220
```

<210> SEQ ID NO 8
<211> LENGTH: 228
<212> TYPE: PRT
<213> ORGANISM: Zea mays

<400> SEQUENCE: 8

```
Met Ala Arg Glu Arg Glu Ile Lys Arg Ile Glu Ser Ala Ala Ala
 1               5                  10                  15

Arg Gln Val Thr Phe Ser Lys Arg Arg Gly Leu Phe Lys Lys Ala
                20                  25                  30

Glu Glu Leu Ser Val Leu Cys Asp Ala Asp Val Ala Leu Ile Val Phe
                35                  40                  45

Ser Ser Thr Gly Lys Leu Ser Gln Phe Ala Ser Ser Ser Met Asn Glu
                50                  55                  60

Ile Ile Asp Lys Tyr Ser Thr His Ser Lys Asn Leu Gly Lys Ala Glu
 65                  70                  75                  80

Gln Pro Ser Leu Asp Leu Asn Leu Glu His Ser Lys Tyr Ala Asn Leu
                85                  90                  95

Asn Glu Gln Leu Val Glu Ala Ser Leu Arg Leu Arg Gln Met Arg Gly
                100                 105                 110

Glu Glu Leu Glu Gly Leu Ser Val Glu Glu Leu Gln Gln Leu Glu Lys
                115                 120                 125

Asn Leu Glu Ser Gly Leu His Arg Val Leu Gln Thr Lys Asp Gln Gln
```

```
                130                 135                 140
Phe Leu Glu Gln Ile Ser Asp Leu Glu Gln Lys Ser Thr Gln Leu Ala
145                 150                 155                 160

Glu Glu Asn Arg Gln Leu Arg Asn Gln Val Ser His Ile Pro Pro Val
                165                 170                 175

Gly Lys Gln Ser Val Ala Asp Thr Glu Asn Val Ile Ala Glu Asp Gly
                180                 185                 190

Gln Ser Ser Glu Ser Val Met Thr Ala Leu His Ser Gly Ser Ser Gln
                195                 200                 205

Asp Asn Asp Asp Gly Ser Asp Val Ser Leu Lys Leu Gly Leu Pro Cys
210                 215                 220

Val Ala Trp Lys
225

<210> SEQ ID NO 9
<211> LENGTH: 228
<212> TYPE: PRT
<213> ORGANISM: Zea mays

<400> SEQUENCE: 9

Met Ala Arg Glu Arg Glu Ile Lys Arg Ile Glu Ser Ala Ala Ala
1               5                   10                  15

Arg Gln Val Thr Phe Ser Lys Arg Arg Gly Leu Phe Lys Lys Ala
                20                  25                  30

Gln Glu Leu Ser Val Leu Cys Asp Ala Asp Val Ala Leu Ile Val Phe
                35                  40                  45

Ser Ser Thr Gly Lys Leu Ser Gln Phe Ala Ser Ser Met Asn Glu
50                  55                  60

Ile Ile Asp Lys Tyr Asn Thr His Ser Lys Asn Leu Gly Lys Thr Glu
65                  70                  75                  80

Gln Pro Ser Leu Asp Leu Asn Leu Glu His Ser Lys Tyr Ala Asn Leu
                85                  90                  95

Asn Glu Gln Leu Ala Glu Ala Ser Leu Arg Leu Arg Gln Met Arg Gly
                100                 105                 110

Glu Glu Leu Glu Gly Leu Asn Val Glu Glu Leu Gln Gln Leu Glu Lys
                115                 120                 125

Asn Leu Glu Ser Gly Leu His Arg Val Leu Gln Thr Lys Asp Ser Gln
                130                 135                 140

Phe Leu Glu Gln Ile Asn Asp Leu Glu Arg Lys Ser Thr Gln Leu Ala
145                 150                 155                 160

Glu Glu Asn Met Gln Leu Arg Asn Gln Val Ser Gln Ile Pro Pro Ala
                165                 170                 175

Gly Lys Gln Ala Val Ala Asp Thr Glu Asn Val Ile Ala Glu Gly Gly
                180                 185                 190

Gln Ser Ser Glu Ser Val Met Thr Ala Leu His Ser Gly Ser Ser Gln
                195                 200                 205

Asp Asn Asp Gly Gly Ser Asp Val Ser Leu Lys Leu Gly Leu Pro Cys
210                 215                 220

Val Ala Trp Lys
225

<210> SEQ ID NO 10
<211> LENGTH: 205
<212> TYPE: PRT
<213> ORGANISM: Zea mays
```

<400> SEQUENCE: 10

```
Arg Asn Gly Leu Leu Lys Lys Ala Tyr Glu Leu Ser Val Leu Cys Asp
 1               5                   10                  15

Ala Glu Val Gly Leu Val Val Phe Ser Ala Thr Gly Lys Leu Phe His
            20                  25                  30

Phe Ala Ser Ser Met Lys Gln Val Ile Asp Arg Tyr Asp Ser His
        35                  40                  45

Ser Lys Thr Leu Gln Arg Ser Glu Pro Gln Ser Ser Gln Leu Gln Ser
50                  55                  60

His Met Asp Asp Gly Thr Cys Ala Arg Leu Lys Glu Glu Leu Ala Glu
65                  70                  75                  80

Thr Ser Leu Lys Leu Arg Gln Met Arg Gly Glu Glu Leu Gln Arg Leu
                85                  90                  95

Ser Val Glu Gln Leu Gln Glu Leu Glu Lys Thr Leu Glu Ser Gly Leu
                100                 105                 110

Gly Ser Val Leu Lys Thr Lys Ser Gln Lys Ile Leu Asp Glu Ile Ser
            115                 120                 125

Gly Leu Glu Arg Lys Arg Thr Gln Leu Ile Glu Glu Asn Ser Arg Leu
130                 135                 140

Lys Glu Gln Val Thr Arg Met Ser Arg Met Glu Thr Gln Leu Gly Ala
145                 150                 155                 160

Asp Pro Glu Phe Val Tyr Glu Glu Gly Gln Ser Ser Glu Ser Val Thr
                165                 170                 175

Asn Thr Ser Tyr Pro Arg Pro Ser Asp Thr Asp Cys Ser Asp
            180                 185                 190

Thr Ser Leu Arg Leu Gly Leu Pro Leu Phe Ser Ser Lys
            195                 200                 205
```

<210> SEQ ID NO 11
<211> LENGTH: 147
<212> TYPE: PRT
<213> ORGANISM: Artificial Sequence
<220> FEATURE:
<223> OTHER INFORMATION: Consensus Sequence

<400> SEQUENCE: 11

```
Asp Lys Tyr Thr His Ser Lys Asn Leu Gly Lys Ser Glu Gln Pro Ser
 1               5                   10                  15

Leu Asp Leu Asn Leu Glu His Ser Lys Tyr Ala Leu Asn Glu Gln Leu
            20                  25                  30

Ala Glu Ala Ser Leu Arg Leu Arg Gln Met Arg Gly Glu Glu Leu Glu
        35                  40                  45

Gly Leu Ser Val Glu Glu Leu Gln Leu Glu Lys Asn Leu Glu Ala
50                  55                  60

Gly Leu His Arg Val Leu Thr Lys Asp Gln Gln Phe Met Glu Gln Ile
65                  70                  75                  80

Ser Glu Leu Arg Lys Thr Gln Leu Ala Glu Asn Arg Leu Arg Asn
                85                  90                  95

Gln Val Ser Gln Ile Ala Gly Val Ala Asp Thr Glu Asn Val Val Glu
                100                 105                 110

Glu Gly Gln Ser Ser Glu Ser Val Met Thr Ala Leu His Ser Gly Ser
            115                 120                 125
```

```
-continued

Ser Gln Asp Asn Asp Asp Gly Ser Asp Val Ser Leu Lys Leu Gly Leu
    130                 135                 140

Pro Ala Lys
145
```